United States Patent [19]
Sohda et al.

[11] Patent Number: 6,147,099
[45] Date of Patent: Nov. 14, 2000

[54] OXAZOLIDINEDIONE DERIVATIVES, THEIR PRODUCTION AND USE

[75] Inventors: Takashi Sohda, Takatsuki; Hitoshi Ikeda, Higashiosaka; Yu Momose, Takarazuka; Sachiko Imai, Kyoto, all of Japan

[73] Assignee: Takeda Chemical Industries, Inc., Osaka, Japan

[21] Appl. No.: 09/292,748

[22] Filed: Apr. 16, 1999

Related U.S. Application Data

[62] Division of application No. 08/832,916, Apr. 4, 1997, Pat. No. 5,972,970, which is a division of application No. 08/554,107, Nov. 6, 1995, Pat. No. 5,665,748, which is a continuation of application No. 08/201,021, Feb. 24, 1994, abandoned.

[30]    Foreign Application Priority Data

Feb. 26, 1993  [JP]  Japan .................................. 5-038236
Aug. 9, 1993   [JP]  Japan .................................. 5-197304

[51] Int. Cl.$^7$ ........................ C07D 277/22; A61K 31/42
[52] U.S. Cl. ........................................ 514/365; 548/203
[58] Field of Search ..................... 548/227, 182, 548/203; 514/365, 374

[56] References Cited

U.S. PATENT DOCUMENTS

| | | | |
|---|---|---|---|
| 4,430,337 | 2/1984 | Holland | 548/227 |
| 5,037,842 | 8/1991 | Goldstein | 514/375 |
| 5,232,925 | 8/1993 | Hindley | 514/272 |

FOREIGN PATENT DOCUMENTS 0 428 312  5/1991  European Pat. Off. .

WO92/02520  2/1992  WIPO .

OTHER PUBLICATIONS

Sohda et al., *Chem. Pharm. Bull.* 30(10) 3580–3600 (1982).

Clark et al., *Chemical Abstracts* 115:136086; 1991.

Dow et al., *Chemical Abstracts* 114: 228799; 1991.

*Primary Examiner*—Jane Fan
*Attorney, Agent, or Firm*—Wenderoth, Lind & Ponack, LLP

[57]    ABSTRACT

Novel 2,4-oxazolidinedione compounds of the formula:

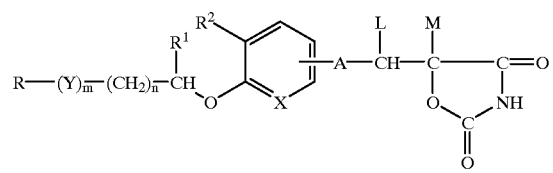

wherein R is a hydrocarbon residue or a heterocyclic group each of which may be substituted; Y is —CO—, —CH(OH)— or —NR$^3$— (wherein R$^3$ is an alkyl group which may be substituted); m is 0 or 1; n is 0, 1 or 2; X is CH or N; A is bivalent straight or branched hydrocarbon chain residue having 1 to 7 carbon atoms; R$^1$ and R$^2$ each are hydrogen or an alkyl group, or R and R are combined with each other to form a 5- to 6-membered heterocyclic group optionally containing nitrogen; L and M each are hydrogen, or L and M are combined with each other to form a bond, or pharmaceutically acceptable salts thereof, having excellent hypoglycemic and hypolipidemic activities and are useful as anti-diabetics or hypolipidemic agents.

5 Claims, No Drawings

OXAZOLIDINEDIONE DERIVATIVES, THEIR PRODUCTION AND USE

This application is a divisional application of Ser. No. 08/832,916, filed Apr. 4, 1997, now U.S. Pat. No. 5,972,970, which is a divisional application of Ser. No. 08/554,107, filed Nov. 6, 1995, now U.S. Pat. No. 5,665,748, which is a continuation of application Ser. No. 08/201,021, filed Feb. 24, 1994, now abandoned.

This invention relates to a novel oxazolidinedione derivative having an action of lowering blood sugar and lipid in blood, to a method of producing it and to an agent for the therapy of diabetes, which is useful in the field of pharmaceuticals.

As remedies of diabetes, various biguanide compounds and sulfonylurea compounds have so far been used. However, biguanide compounds are hardly used at present, since they cause lactic acidosis, while sulfonylurea compounds, which have a strong action of lowering blood sugar, often cause severe hypoglycemia, requiring special attention in use. On the other hand, there are thiazolidinedione derivatives and oxazolidinedione derivatives known to have actions of lowering blood sugar and lipid in blood, which are free of such drawbacks.

For example, JPA H3(1991)-170478 and WO9202520-A1 describe, as 2,4-oxazolidinedione derivatives having substituents at the 5-position, a series of 5-(substituted benzyl)-2,4-oxazolidinedione derivatives, JPB S62(1987)-30993 describes 2,4-oxazolidinedione derivatives substituted with alicyclic groups at the 5-position, and JPB S63 (1988)-35632 describes 2,4-oxazolidinedione derivatives substituted with, among others, a substituted aromatic ring at the 5-position.

The present inventors studied extensively on 2,4-oxazolidinedione derivatives, and found that novel derivatives having, as substituents at the 5-position of 2,4-oxazolidinedione ring, a bivalent straight or branched hydrocarbon chain residue substituted with phenyl or pyridyl, e.g. 2-(substituted phenyl or substituted pyridyl) ethyl group, 3-(substituted phenyl or substituted pyridyl) propyl group, 4-(substituted phenyl or substituted pyridyl) butyl group, 5 -(substituted phenyl or substituted pyridyl) pentyl group, etc., possess actions of lowering blood sugar and lipid in blood, thus the present invention being completed.

More specifically, the present invention relates to:
1. a 2,4-Oxazolidinedione derivative represented by the general formula:

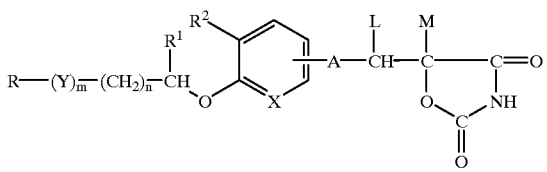

wherein R is a hydrocarbon residue or a heterocyclic group each of which may be substituted; Y is —CO—, —CH(OH) or $NR^3$— (wherein $R^3$ is an alkyl group which may be substituted); m is 0 or 1; n is 0, 1 or 2; X is CH or N; A is bivalent straight or branched hydrocarbon chain residue having 1 to 7 carbon atoms; $R^1$ and $R^2$ each are hydrogen or an alkyl group, or $R^1$ and $R^2$ are combined with each other to form a 5- to 6-membered heterocyclic group optionally containing nitrogen; L and M each are hydrogen, or L and M are combined with each other to form a bond, or a pharmaceutically acceptable salt thereof, 2. a medicinal composition comprising, as an effective component, a 2,4-oxazolidinedione derivative represented by the general formula (I) or a pharmaceutically acceptable salt thereof, 3. a method for treating a mammal suffering from diabetes or hyperlipidemia, which comprises administering to the mammal an effective amount of a compound of the formula (I) or a pharmaceutically acceptable salt thereof, 4. use of a compound of the formula (I) or a pharmaceutically acceptable salt thereof for the manufacture of a medicament for the treatment of a mammal suffering from diabetes or hyperlipidemia, 5. methods of producing a 2,4-oxazolidinedione derivative represented by the general formula (I).

The compounds represented by the general formula (I) include compounds shown by the following formulas (I-A1), (I-A2) and (I-A3).

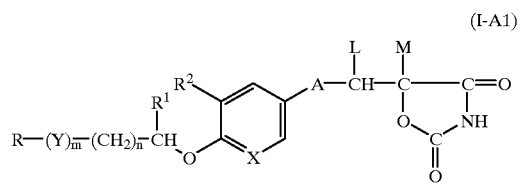

(I-A1)

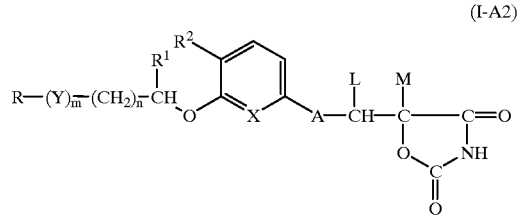

(I-A2)

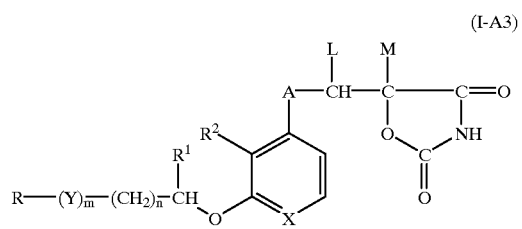

(I-A3)

wherein each symbol has the meaning given above. Among the compounds (I-A1), (I-A2) and (I-A3), compounds (I-A1) and (I-A2) are preferable, and compounds (I-A1) are more preferable, in view of pharmacological activity, toxicity and side effects. Compounds shown by the formula (I) wherein L and M are combined with each other to form a bond, are ones shown by the following formula:

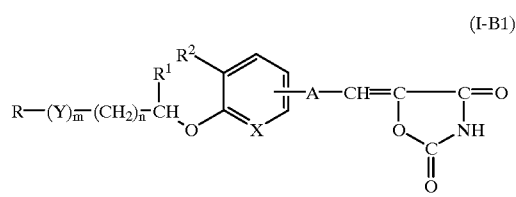

(I-B1)

wherein each symbol has the meaning given above. Compounds shown by the formula (I) wherein L and M each are hydrogen, are ones shown by the following formula:

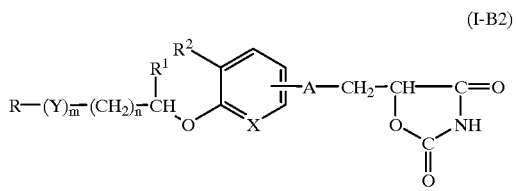
(I-B2)

wherein each symbol has the meaning given above.

In the formula (I), an alkyl group shown by $R^1$ and $R^2$ is one having 1 to 4 carbon atoms, such as methyl, ethyl, n-propyl, i-propyl, n-butyl, t-butyl, etc.

The above mentioned general formula (I-B1) represents both (E)- and (Z)-isomers relative to the double bond at the 5-position of the 2,4-oxazolidinedione ring.

With respect to the above general formula (I), in the case where $R^1$ and $R^2$ combine with each other to form a 5- or 6-membered heterocyclic ring optionally containing N, examples of such compounds include those represented by the following general formulas. (1) $R^1$ and $R^2$ combine with each other to form a 5-membered heterocyclic ring.

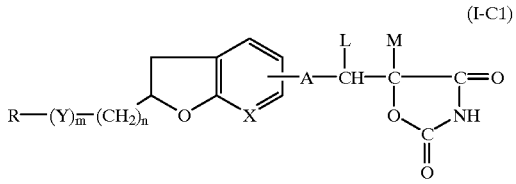
(I-C1)

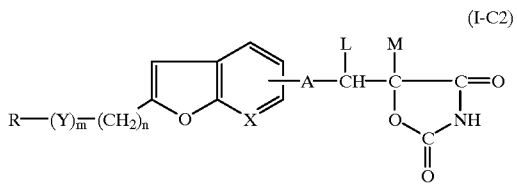
(I-C2)

(2) $R^1$ and $R^2$ combine with each other to form a 6-membered heterocyclic ring.

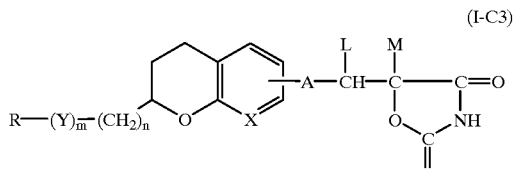
(I-C3)

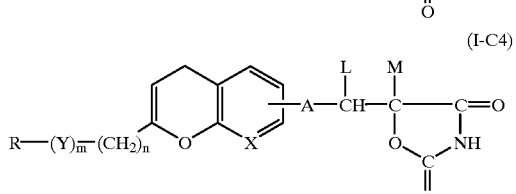
(I-C4)

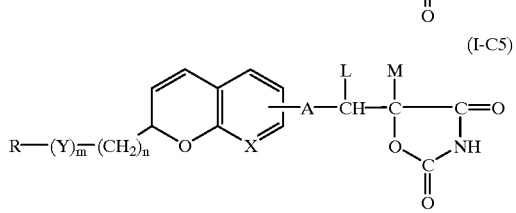
(I-C5)

(3) $R^1$ and $R^2$ combine with each other to form a 5-membered heterocyclic ring containing N.

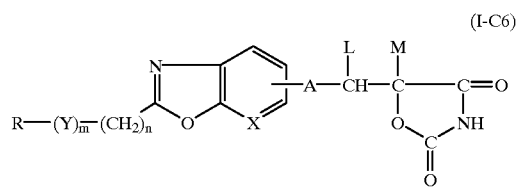
(I-C6)

(4) $R^1$ and $R^2$ combine with each other to form a 6-membered heterocyclic ring containing N

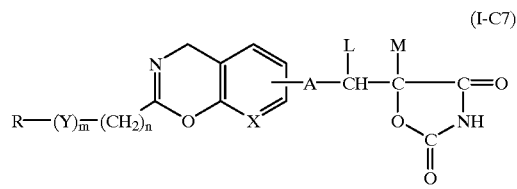
(I-C7)

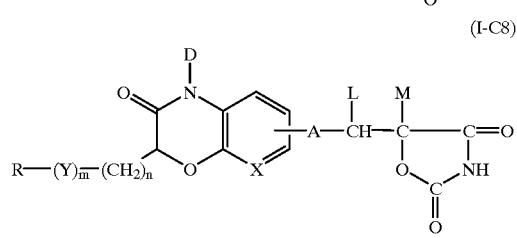
(I-C8)

[wherein D stands for hydrogen or a lower alkyl group, and other symbols have the meanings given above.]

Among the above-mentioned compounds (1-C1) to (I-C8), those represented by (I-C1), (I-C2), (I-C3) and (I-C6) are preferable.

In the above-mentioned general formula (I), as hydrocarbon residues in the hydrocarbon residues which may be substituted shown by R, mention is made of aliphatic hydrocarbon residues, alicyclic hydrocarbon residues, alicyclic-aliphatic hydrocarbon residues, aromatic aliphatic hydrocarbon residues, aromatic hydrocarbon residues and aromatic heterocyclic- aliphatic hydrocarbons. As the aliphatic hydrocarbon residues, mention is made of ones having 1 to 8 carbon atoms including saturated aliphatic hydrocarbon residues having 1 to 8 carbon atoms as exemplified by methyl, ethyl, propyl, isopropyl, butyl, isobutyl, sec.-butyl, t.-butyl, pentyl, isopentyl, neopentyl, t.-pentyl, hexyl, isohexyl, heptyl and octyl, and unsaturated aliphatic hydrocarbon residues having 2 to 8 carbon atoms as exemplified by ethenyl, 1-propenyl, 2-propenyl, 1-butenyl, 2-butenyl, 3-butenyl, 2-methyl-1-propenyl, 1-pentenyl, 2-pentenyl, 3-pentenyl, 4 -pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl. As the alicyclic hydrocarbon residues, mention is made of ones having 3 to 7 carbon atoms including saturated alicyclic hydrocarbon residues having 3 to 7 carbon atoms as exemplified by cyclopropyl, cyclobutyl, cyclopentyl, cyclohexyl and cycloheptyl, and unsaturated alicyclic hydrocarbon residues having 5 to 7 carbon atoms as exemplified by 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl. As the alicyclic-aliphatic hydrocarbon residues, mention is made of, among those formed by combination of the above-mentioned alicyclic hydrocarbon groups with aliphatic hydrocarbon residues, ones having 4 to 9 carbon atoms as exemplified by cycloproptlmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexenylethyl, cyclohexylethyl, cyclohexylpropyl, cycloheptylmethyl and cycloheptylethyl. As the aromatic aliphatic hydrocarbon residues, mention is made of phenylalkyl having 7 to 9 carbon atoms as exemplified by benzyl, phenethyl, 1-phenylethyl, 3-phenylpropyl, 2-phenylpropyl and 1-phenylpropyl, and naphthylalkyl having 7 to 9 carbon atoms as exemplified by α-naphthylmethyl, α-naphthylethyl, β-naphthylmethyl and β-naphthylethyl. As the aromatic hydrocarbon residues, mention is made of, for example, phenyl, naphthyl (α-naphthyl, A-naphthyl), among others. As the aromatic heterocyclic-aliphatic hydrocarbon residues, mention is made of those formed by combination of heterocyclic groups mentioned below with the above-mentioned aliphatic hydrocarbon residues, which are exemplified as follows.

In the above-mentioned general formula (I) as the heterocyclic groups in the substituted heterocyclic groups which may be substituted shown by R, mention is made of, for example, 5- to 7-membered heterocyclic groups containing one sulfur atom, nitrogen atom or oxygen atom, 5- to 6-membered heterocyclic groups containing 2 to 4 nitrogen atoms, and 5- to 6-membered heterocyclic groups containing 1 to 2 nitrogen atoms and one sulfur atom or oxygen atom. These heterocyclic groups are optionally condensed with 6-membered ring containing one or two nitrogen atoms, benzene ring or 5-membered ring containing one sulfur atom. Examples of these heterocyclic groups include 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-triazol-3-yl, 1,3,4-triazol-2-yl, 1,2,3-triazol-4-yl, tetrazol-5-yl, benzimidazol-2-yl, indol-3-yl, benzpyrazol-3-yl, 1H-pyrrolo[2,3-b]pyrazin-6-yl, 1H-imidazo[4,5-b]pyridin-2-yl, 1H-imidazo[4,5-c]pyridin-2-yl, and 1H-imidazo[4,5-b]pyrazin-2-yl, etc.

In the above-mentioned general formula (I) the hydrocarbon residue and heterocyclic residue shown by R optionally have 1 to 3 substituents at substitutable positions, respectively. As such substituents, mention is made of aliphatic chain hydrocarbon group, alicyclic hydrocarbon group, aryl group, aromatic heterocyclic group, non-aromatic heterocyclic group, halogen atom, nitro group, optionally substituted amino group, optionally substituted acyl group, optionally substituted hydroxyl group, optionally substituted thiol group and optionally esterified carboxyl group.

As the aliphatic chain hydrocarbon group, mention is made of straight-chain or branched aliphatic hydrocarbon groups having 1 to 15 carbon atoms, for example, alkyl group, preferably alkyl group having 1 to 10 carbon atoms, alkenyl group, preferably alkenyl group having 2 to 10 carbon atoms, and alkynyl group, preferably alkynyl group having 2 to 10 carbon atoms.

Preferable examples of the alkyl group include methyl, ethyl, propyl, isopropyl, butyl, isobutyl, sec-butyl, tert-butyl, pentyl, isopentyl, neopentyl, tert-pentyl, 1-ethyl propyl, hexyl, isohexyl, 1,1-dimethylbutyl, 2,2-dimethylbutyl, 2,2-dimethylbutyl, 3,3-dimethylbutyl, 2-ethylbutyl, hexyl, pentyl, octyl, nonyl and decyl. Preferable examples of the alkenyl group include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl and 5-hexenyl. Preferable examples of the alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, .2-hexynyl, 3-hexynyl, 4-hexynyl and 5-hexynyl. As the alicyclic hydrocarbon group, mention is made of saturated or unsaturated alicyclic hydrocarbon groups having 3 to 12 carbon atoms, for example, cycloalkyl group, cycloalkenyl group and cycloalkadienyl group. Preferable examples of cycloalkyl group include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.1]nonyl, bicyclo[3.3.1]nonyl, bicyclo[4.2.1]nonyl and bicyclo[4.3.1]decyl, etc. Preferable examples of cycloalkenyl group include 2-cyclopenten-1-yl, 3-cyclopenten-1-yl, 2-cyclohexen-1-yl and 3-cyclohexen-1-yl. As preferable examples of cycloalkadienyl group include 2,4-cyclopentadien-1-yl, 2,4-cyclohexadien-1-yl and 2,5-cyclohexadien-1-yl. The said aryl group means monocyclic or condensed polycyclic aromatic hydrocarbon groups. Preferable examples of the aryl group include ones having 6 to 14 carbon atoms such as phenyl, naphthyl, anthryl, phenanthryl and acenaphthylenyl. Among them, phenyl 1-naphthyl and 2-naphthyl are preferable.

Preferable examples of the aromatic heterocyclic group include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl; and aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a)pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl, etc.

Preferable examples of the non-aromatic heterocyclic group include oxiranyl, azetidinyl, oxetanyl, thietanyl, pyrrolidinyl, tetrahydrofuryl, thiolanyl, piperidyl, tetrahydropyranyl, morpholinyl, thiomorpholinyl, pyrrolidino, piperidino, morpholino and piperazinyl. Examples of the halogen include fluorine, chlorine, bromine and iodine. Among them, fluorine and chlorine are especially preferable. The optionally substituted includes unsubstituted amino group and substituted amino group. As the substituted amino group, mention is made of amino group (—NH$_2$) on which one or two of alkyl having 1 to 10 carbon atoms, alkenyl having 1 to 10 carbon atoms, aromatic group or acyl group having 2 to 10 carbon atoms (e.g. methylamino, dimethylamino, ethylamino, diethylamino, dibutylamino, diallylamino, cyclohexylamino, phenylamino, N-methyl-N-phenylamino, acetylamino, propionylamino, and benzoylamino etc.) is substituted. The optionally substituted acyl group includes unsubstituted acyl group and substituted acyl groups. As the unsubstituted acyl group, mention is made of formyl and those formed by condensation of ($C_1$–$C_{10}$)alkyl, ($C_1$–$C_{10}$)alkenyl or ($C_6$–$C_{12}$)aromatic group with carbonyl group (e.g. acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl and nicotinoyl). The substituted acyl group includes acyl groups mentioned above in connection with unsubstituted acyl group which have substituent(s) such as an alkyl having 1 to 3 carbon atoms, an alkoxy having 1 to 3 carbon atoms, halogen (e.g. chlorine, bromine etc.), nitro hydroxy, amino etc. The optionally substituted hydroxyl group includes unsubstituted hydroxyl group and substituted hydroxyl groups. As the substituted hydroxyl group, mention is made of such ones as having, on this hydroxyl group, a suitable substituent, especially the one employable as a hydroxyl-protecting group, as exemplified by besides alkoxy, alkenyloxy, aralkyloxy, acyloxy and aryloxy. Preferable examples of the alkoxy include ones having 1 to 10 carbon atoms (e.g. methoxy, ethoxy, propoxy, isopropoxy, butoxy, isobutoxy, sec-butoxy, tert-butoxy, pentoxy, isopentoxy, neopentoxy, hexyloxy, heptyloxy, nonyloxy, cyclobutoxy, cyclopentoxy and cyclohexyloxy). As alkenyloxy, mention is made of ones having 1 to 10 carbon atoms including, for example, allyloxy, crotyloxy, 2-pentenyloxy, 3-hexenyloxy, 2-cyclopentenylmethoxy and 2-cyclohexenylmethoxy, and, as aralkyloxy, mention is made of, for example, phenyl-($C_1$–$C_4$)alkyloxy (e.g. benzyloxy and phenethyloxy). Preferable examples of acyloxy include alkanoyloxy having 2 to 4 carbon atoms (e.g. acetyloxy, propionyloxy, n-butyryloxy and iso-butyryloxy). As aryloxy, mention is made of 4-chlorophenoxy, among others.

As the optionally substituted thiol group, mention is made of, besides thiol group, such ones as having, on this thiol group, a suitable substituent, especially the one employable as a thiol-protecting group, as exemplified by alkylthio, aralkylthio and acylthio. Preferable examples of the alkylthio include alkylthio having 1 to 10 carbon atoms (e.g. methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio and cyclohexylthio. As aralkylthio, mention is made of, for example, phenyl-($C_1$–$C_4$)alkylthio (e.g. benzylthio and phenethylthio). Preferable examples of acylthio include alkanoylthio having 2 to 4 carbon atoms (e.g. acetylthio, propionylthio, n-butyrylthio and iso-butyrylthio). As the optionally esterified carboxyl group, mention is made of, for example, alkoxycarbonyl (e.g. ones having 2 to 5 carbon atom such as methoxycarbonyl, ethoxycarbonyl, propoxycarbonyl and butoxycarbonyl), aralkyloxycarbonyl (e.g. benzyloxycarbonyl) and aryloxycarbonyl (e.g. phenoxycarbonyl and p-tolyloxycarbonyl).

In the above-mentioned general formula (I) substituents on the hydrocarbon residue and heterocyclic group shown by R may, when they are alicyclic hydrocarbon group, aryl group, aromatic heterocyclic group or non-aromatic heterocyclic group, have one or more, preferably 1 to 3, of suitable substituents respectively. Examples of these substituents include lower alkyl groups having 1 to 4 carbon atoms, lower alkenyl groups having 2 to 5 carbon atoms, lower alkynyl groups having 2 to 5 carbon atoms, cycloalkyl groups having 3 to 7 carbon atoms, aryl groups (e.g. phenyl, naphthyl, etc.), aromatic heterocyclic groups (e.g. thienyl, funyl, pyridyl, oxazolyl, thiazolyl, etc.), non-aromatic heterocyclic groups, (e.g. tetrahydrofuryl, morpholino, piperidino, pyrrolidino, piperazino, etc.), aralkyl groups having 7 to 9 carbon atoms, amino group, n-mono-($C_1$–$C_4$) alkyl amino groups, N,N-di($C_1$–$C_4$)alkyl amino groups, amidino groups, acyl group having 2 to 5 carbon atoms, carbamoyl group, N-mono-($C_1$–$C_4$)alkyl carbamoyl groups, N,N-di($C_1$–$C_4$)alkyl carbamoyl group, sulfamoyl group, N-mono($C_1$–$C_4$)alkyl sulfamoyl groups, N,N-di($C_1$–$C_4$) alkylsulfamoyl groups, carboxyl group, lower alkoxycarbonyl groups having 2 to 5 carbon atoms, hydroxyl group, lower alkoxy groups having 1 to 4 carbon atoms, lower alkenyloxy groups having 2 to 5 carbon atoms, cycloalkyloxy groups having 3 to 7 carbon atoms, aralkyloxy groups having 7 to 9 carbon atoms, aryloxy groups (e.g. phenyloxy, naphthyloxy, etc.), mercapto group, lower alkylthio groups having 1 to 4 carbon atom, aralkylthio groups having 7 to 9 carbon atoms, arylthio groups (e.g. phenylthio, naphthylthio, etc.), sulfo group, cyano group, azide group, nitro group, nitroso group and halogen (e.g. fluorine, chlorine, bromine, iodine).

In the above formula (I), when each m and n is 0, carbon substituted by $R^1$ is directly bonded to R; when m is 0 and n is 1 or 2, R is directly bonded to -$(CH_2)_n$—; and when m is 1 and n is 0, Y is directly bonded to the carbon substituted by $R^1$.

Y is —CO—, —CH(OH)— or —N($R^3$)—, preferably —CH(OH)— or —N(R )—. The alkyl group shown by R is one having 1 to 4 carbon atoms, such as methyl, ethyl, n-propyl, i-propyl, n-butyl, t-butyl, etc. As the substituent of the alkyl, a halogen atom (e.g. fluorine, chlorine, bromine, iodine), an alkoxy group having 1 to 4 carbon atoms, (e.g. methoxy, ethoxy, propoxy, n-butoxy, t-butoxy, etc.), hydroxyl, nitro, an acyl group having 1 to 4 carbon atoms (e.g. formyl, acetyl, propionyl, etc.) are mentioned.

The bivalent straight or branched hydrocarbon chain residue shown by A includes saturated one (i.e. —$CH_2$—, —$(CH_2)_2$—, —$CH(CH_3)$—, —$(CH_2)_3$—, —$CH(C_2H_5)$—, —$(CH_2)_4$, —$(CH_2)_5$, —$(CH_2)_6$ and —$(CH_2)_7$—] and unsaturated one (e.g. —CH=CH—, —$C(CH_3)$=CH—, —CH=CH—$CH_2$—, —$C(C_2H_5)$=CH—, —$CH_2$—CH=CH—$CH_2$—, —$CH_2$—$CH_2$—CH=CH—$CH_2$—, —CH=CH—CH=CH—$CH_2$—, —CH=CH—CH=CH—$CH_2$—.

In the formula (I-C8), the alkyl group shown by D is one having 1 to 4 carbon atoms such as methyl, ethyl, n-propyl, i-propyl, n-butyl.

As salts of the compound (I) of this invention, pharmaceutically acceptable ones are preferable, as exemplified by salts with an inorganic base, salts with an organic base, salts with an inorganic acid, salts with an organic acid, and salts with an basic or acidic amino acid. Preferable examples of salts with an inorganic base include alkali metal salts such as sodium salts and potassium salts; alkaline earth metal salts such as calcium salts and magnesium salts; and aluminum salts, ammonium salts or the like. Preferable examples of salts with an organic base include those with, for example, trimethylamine, triethylamine, pyridine, picoline, ethanolamine, diethanolamine, triethanolamine, dicyclohexylamine and N,N'-dibenzylethylenediamine. Preferable examples of salts with an inorganic acid include those with, for example, hydrochloric acid, hydrobromic acid, nitric acid, sulfuric acid or phosphoric acid. Preferable examples of salts with an organic acid include those with, for example, formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. Preferable examples of salts with a basic amino acid include those with, for example, arginine, lysine and ornithine, and, preferable examples of salts with an acidic amino acid include those with, for example, aspartic acid and glutamic acid. Among them, sodium salt or potassium salt is more preferable.

The compound (I) or its pharmaceutically acceptable salts of the present invention possess an action of lowering blood sugar with low toxicity, which can be used as such or in a composition with, for example, a per se known pharmacologically acceptable carrier, excipient and filler as a therapeutic agent of diabetes in mammals including man. Compound (I) or pharmaceutically acceptable salt thereof of the present invention also exhibits improving activity of insulin resistance and can also be used as a hypotensor.

The compound (I) of this invention is low in toxicity. For example, oral administration of the compound of Example 18 at a dose of 15 mg/kg/day for 4 days to mice caused no change in body weight and liver weight in comparison with the control group. And, oral administration of the compound produced in Example 18 at a dose of 100 mg/kg or intraperitoneal administration at a dose of 50 mg/kg killed no test animals.

The administration is usually performed orally in the form of, for example, tablets, capsules (including soft capsules and microcapsules), powders and granules, and, depending on cases, non-orally in the form of, for example, injections, suppositories and pellets. The dosage for adults in the case of oral administration ranges from 0.05 to 10 mg/kg per day, desirably once to three times a day.

The compound (I) of this invention, mixed with pharmaceutically acceptable carriers, can be administered orally or non-orally in the form of solid preparations such as tablets, capsules, granules and powders; or in the form of liquid preparations such as syrups and injections.

As pharmaceutically acceptable carriers, use is made of conventional organic or inorganic carriers for pharmaceutical preparations, more specifically, for example, excipients, lubricants, binders and disintegrators for solid preparations; and solvents, solubilizers, suspending agents, isotonizers, buffering agents and local anesthetic agents. And, upon necessity, such additives as antiseptics, anti-oxidants, colorants and sweeteners are further used. Preferable examples of excipients include lactose, sucrose, D-mannitol, starch, crystalline cellulose and light silicon dioxide. Preferable examples of lubricants include magnesium stearate, calcium stearate, talc and colloid silica. Preferable examples of binders include crystalline cellulose, sugar, D-mannitol, dextrin, hydroxypropyl cellulose, hydroxypropyl methyl cellulose and polyvinyl pyrrolidone. Preferable examples of disintegrators include starch, carboxymethyl cellulose, carboxymethyl-cellulose calcium, crosscarmelose sodium and carboxymethyl starch sodium. Preferable examples of solvents include distilled water for injection, alcohol, propylene glycol, macrogol, sesame oil and corn oil. Preferable examples of solubilizers include polyethylene glycol, propylene glycol, D-mannitol, benzyl benzoate, ethanol, trisamino methane, cholesterol, triethanolamine, sodium carbonate and sodium citrate. Preferable examples of suspending agents include surfactants such as stearyl triethanolamine, sodium lauryl sulfate, lauryl aminopropionate, lecithin, benzalkonium chloride, benzethonium chloride, glycerin monostearate; and hydrophilic polymers such as polyvinyl alcohol, polyvinyl pyrrolidone, sodium carboxymethyl cellulose, methylcellulose, hydroxymethylcellulose, hydroxyethylcellulose and hydroxypropylcellulose. Preferable examples of isotonizers include sodium chloride, glycerin and D-mannitol. Preferable examples of buffering agents include buffer solutions of phosphates, acetates, carbonates and citrates. Preferable examples of local anesthetic agents include benzyl alcohol. Preferable examples of antiseptics include paraoxybenzoic acid esters, chlorobutanol, benzyl alcohol, phenethyl alcohol, dehydroacetic acid and sorbic acid. Preferable examples of anti-oxidants include sulfites and ascorbic acid.

The following is the description on the method of producing the compound (I) of this invention.

Method A

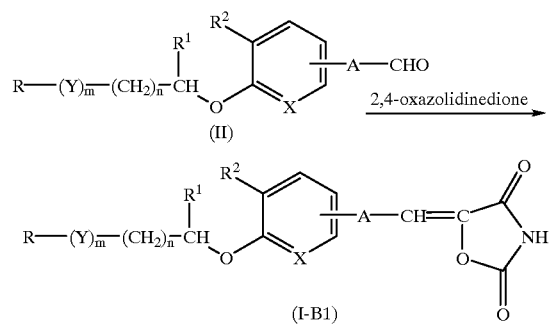

[wherein each symbol has the same meaning as defined above].

The compound (I-B1) can be produced by condensation of the compound (II) with 2,4-oxazolidinedione. This reaction is conducted in a solvent in the presence of a base. As the solvent, mention is made of alcohols such as methanol, ethanol, propanol, isopropanol and 2-methoxyethanol; aromatic hydrocarbons such as benzene, toluene and xylene; ethers such as ethyl ether, isopropyl ether, dioxane and tetrahydrofuran; N,N-dimethylformamide, dimethyl sulfoxide and acetic acid. As the base, use is made of sodium alkoxide (e.g. sodium methoxide, sodium ethoxide, etc.), potassium carbonate, sodium carbonate, sodium hydride, sodium acetate or a secondary amine such as piperidine, piperazine, pyrrolidine, morpholine, diethylamine, diisopropylamine, among others. The amount of 2,4-oxazolidinedione to be used ranges from 1 to 10 molar equivalents, preferably 1 to 5 molar equivalents, relative to the compound (II). The amount of the base to be used ranges from 0.01 to 5 molar equivalents, preferably 0.05 to 2 molar equivalents, relative to the compound (II). This reaction is conducted at temperatures ranging from 0 to 150° C, preferably from 20 to 100° C., over a period ranging from 0.5 to 30 hours.

The compound (I-B1) to be produced by the above method is, in some instances, obtained as a mixture of (E)-compound and (Z)-compound, relative to the double bond at 5-position of the 2,4-oxazolidinedione ring.

Method B

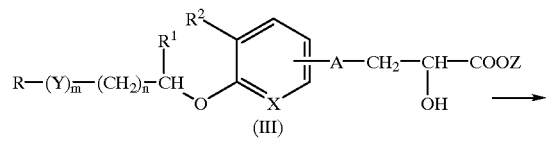

-continued

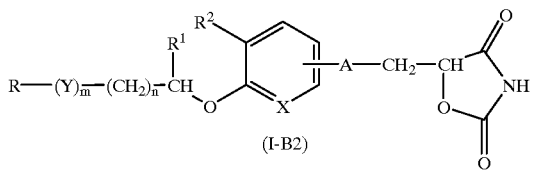

(I-B2)

(wherein Z is hydrogen, a lower alkyl group or an aralkyl group, and other symbols have the meanings given above.)

In the above-mentioned general formula (III), as the lower alkyl group shown by Z, mention is made of alkyl havaing 1 to 4 carbon atoms (e.g. methyl, ethyl, propyl, isopropyl, butyl, isobutyl, sec-butyl and tert-butyl). The aralkyl group shown by Z means an alkyl group having aryl group as the substituent. Examples of the aryl group include phenyl and naphthyl, which may optionally be substituted with the afore-mentioned alkyl groups having 1 to 4 carbon atoms, halogen atoms (e.g. fluorine, chlorine, bromine, iodine), hydroxyl group and nitro group. As the alkyl moiety of the aralkyl group, alkyls having 1 to 4 carbon atoms such as methyl, ethyl, propyl, etc. are mentioned. Preferable examples of the aralkyl group include benzyl, phenethyl, 3-phenylpropyl, (1-naphthyl)methyl and (2-naphthyl) methyl, etc. Among them, benzyl and phenethyl are preferable.

An alkali metal salt of the compound (I-B2) can be produced by allowing a compound (III) to react with an alkali metal cyanate such as potassium cyanate or sodium cyanate. Then, the alkali metal salt is treated with an acid to produce the compound (I-B2). The reaction of the compound (III) with the alkali metal cyanate is conducted in an adequate solvent. As the solvent, use is generally made of alcohols such as methanol, ethanol, propanol, isopropanol, 2-methoxyethanol and butanol, N,N-dimethylformamide, dimethyl sulfoxide, acetonitrile or a suitable mixture of them. The amount of the alkali metal cyanate to be used ranges from 1 to 10 molar equivalents, preferably 1 to 5 molar equivalents. The reaction temperature ranges from 0 to 150° C., preferably from 10 to 120° C., and the reaction time ranges from 0.5 to 50 hours. The alkali metal salt of the compound (I-B2) thus obtained is treated with an acid by a conventional means to produce the compound (I-B2). This acid treatment is conducted in the presence or absence of a suitable solvent. Examples of the solvent include alcohols such as methanol, ethanol, propanol, isopropanol, 2-methoxyethanol and butanol; aromatic hydrocarbons such as benzene, toluene and xylene; ethers such as ethyl ether, isopropyl ether, dioxane and tetrahydrofuran; halogenated hydrocarbons such as chloroform, dichloromethane and 1,1,2,2-tetrachloroethane; ethyl acetate, acetonitrile or a mixture of them. As the acid, use is preferably made of an excess amount of an inorganic acid such as hydrochloric acid, sulfuric acid, nitric acid and hydrobromic acid, while an organic acid such as acetic acid, citric acid, tartaric acid or the like can also be used.

Thus obtained 2,4-oxazolidinedione derivative (I-B2) can be isolated and purified by a known isolating and purifying means such as concentration, concentration under reduced pressure, solvent extraction, crystallization, recrystallization, phasic transfer, chromatography or the like.

Method C

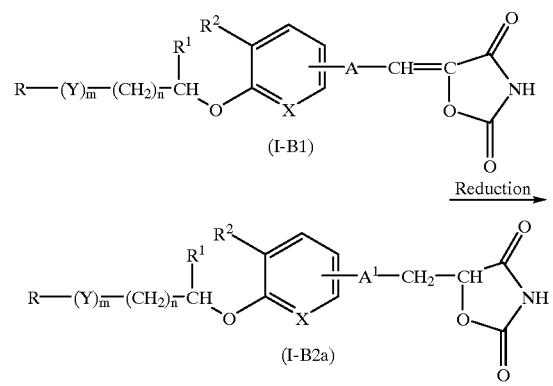

(wherein $A^1$ is a saturated bivalent straight or branched hydrocarbon chain residue having 1 to 7 carbon atoms, and other symbols have the meanings given above.)

The saturated bivalent straight or branched hydrocarbon chain residue having 1 to 7 carbon atom shown by A is the saturated one given as the definition of A.

By subjecting the compound (I-B1) to reduction, the compound (I-B2a) can be produced. This reduction is conducted, in accordance with a conventional method, in the presence of a catalyst under hydrogen atmosphere of 1 to 150 atmospheric pressure. As the solvent, mention is made of alcohols such as methanol, ethanol, propanol, isopropanol and 2-methoxyethanol, aromatic hydrocarbons such as benzene, toluene and xylene, ethers such as ethyl ether, isopropyl ether, dioxane and tetrahydrofuran, halogenated hydrocarbons such as chloroform dichloromethane and 1,1,2,2-tetrachloroethane, ethyl acetate, acetic acid, N,N-dimethylformamide or a suitable mixture of them. Examples of preferable catalysts include metals such as nickel compounds and transition metals such as palladium, platinum and rhodium. Reaction temperatures range from 0 to 100° C., preferable from 10 to 80° C. Reaction time ranges from 0.5 to 50 hours. The 2,4-oxazolidinedione derivative (I-B2a) thus obtained can be isolated and purified by a known refining means such as concentration, concentration under reduced pressure, solvent extraction, crystallization, recrystallization, phasic transfer and chromatography.

Method D

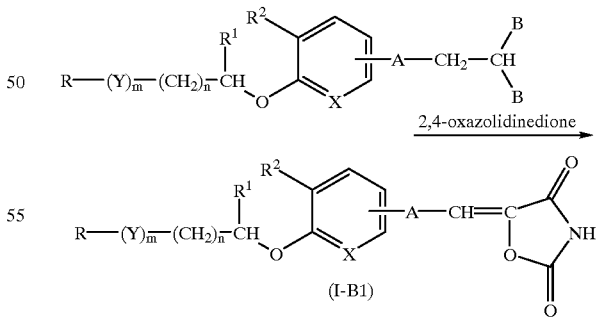

[wherein B stands for lower alkoxy, lower alkylthio or lower acyloxy; and other symbols are of the same meaning as defined above].

As the lower alkoxy, lower alkylthio and lower acyloxy, respectively shown by B, mention is made of, for example, ones having 1 to 4 carbon atoms such as methoxy, ethoxy, propoxy, isopropoxy and butoxy; ones having 1 to 4 carbon atoms such as methyl thio, ethylthio, propylthio, i-propylthio and butylthio; ones having 1 to 4 carbon atoms such as acetyloxy and propionyloxy, respectively. Depending cases, two B's may be combined to each other to form, for example, ethylenedioxy, propylenedioxy or dithiotrimethylene. In other words, —CH(B)$_2$ of the formula (IV) means a protected aldehyde group.

The compound (IV) is condensed with 2,4-oxazolidinedione to produce a compound (I-B1). This condensation reaction is conducted substantially the same manner as in the reaction of the compound (II) with 2,4-oxazolidinedione in Method A.

Method E

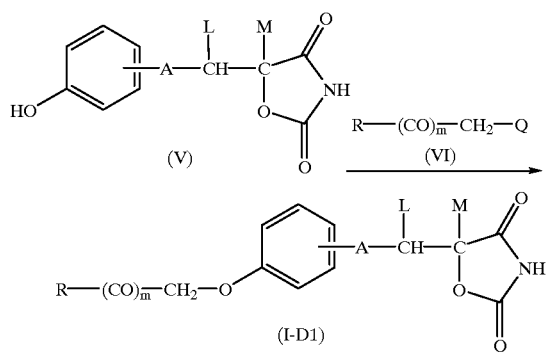

(V)    (VI)    (I-D1)

[wherein Q is a leaving group and other symbols are of the same meaning as defined above]

As the leaving group shown by Q, mention is made of a halogen (e.g. chlorine, bromine, iodine), methanesulfonyloxy, benzenesulfonyloxy and p-toluenesulfonyloxy.

The compound (V) is condensed with the compound (VI) to produce a compound (I-DI). This reaction is conducted, in accordance with a conventional method, in an adequate solvent in the presence of a base. Examples of the solvent include aromatic hydrocarbon such as benzene, toluene and xylene; ethers such as dioxane, tetrahydrofuran and dimethoxyethane; ketones such as acetone and 2-butanone; N,N-dimethylformamide, dimethyl sulfoxide, chloroform, dichloromethane, 1,2-dichloroethane, 1,1,2,2-tetrachloroethane; and a suitable mixture of these solvents. As the base, mention is made of alkali metal salt such as sodium hydroxide, potassium hydroxide, potassium carbonate and sodium hydrogencarbonate; amines such as pyridine, triethylamine, N,N-dimethylaniline; metal hydroxide such as sodium hydroxide and potassium hydroxide; sodium ethoxide, sodium methoxide and potassium t-butoxide, among others. The amount of these bases to be used is preferably in a range of from about 1 to 5 mol. relative to the compound (V). This reaction is conducted usually at temperatures ranging from −50° C. to 150° C., preferably from about −10° C. to 100° C. The reaction time ranges from 0.5 to 30 hours.

The starting compound of Method A can for example be prepared by Method F.

Method F

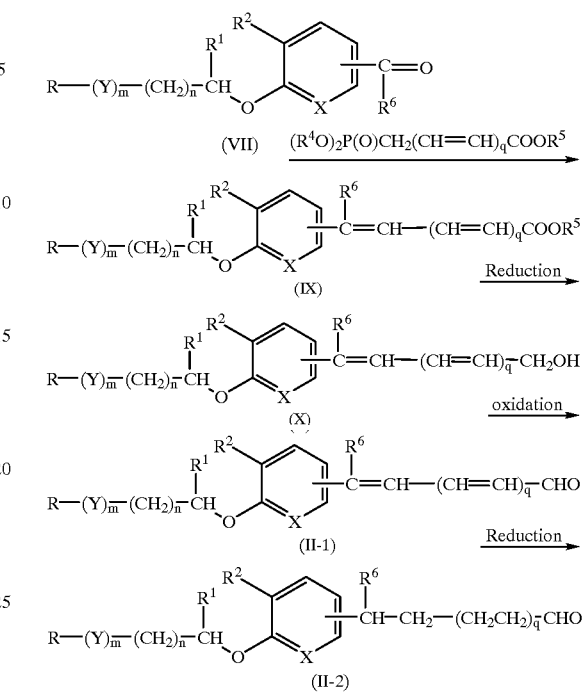

[wherein $R^4$ and $R^5$ independently stand for a lower alkyl group; $R^6$ stands for hydrogen or a lower alkyl group; q denotes 0, 1 or 2; and other symbols are of the same meaning as defined above].

Examples of the lower alkyl groups shown by $R^4$, $R^5$ and $R^6$ include ones having 1 to 4 carbon atoms such as methyl, ethyl, propyl, isopropyl and butyl.

In this method, first, a formyl or a acyl derivative (VII) is allowed to react with a phosphonoacetic acid derivative or a Ω-phosphonocarboxylic acid derivative (VIII) to produce an unsaturated ester derivative (IX). The reaction of (VII) with (VIII) is conducted, in accordance with a conventional method, in an adequate solvent in the presence of a base. Examples of the solvent include aromatic hydrocarbon such as benzene, toluene and xylene; ethers such as dioxane, tetrahydrofuran and dimethoxyethane; alcohols such as methanol, ethanol and propanol; N,N-dimethylformamide, dimethyl sulfoxide, chloroform, dichloromethane, 1,2, dichloroethane and 1,1,2 2-tetrachloroethane, as well as a suitable mixture of them. Examples of the base include alkali metal salts such as sodium hydroxide, potassium hydroxide, potassium carbonate, sodium carbonate and sodium hydrogencarbonate; amines such as pyridine, triethylamine and N,N-dimethyl aniline; metal hydrides such as sodium hydride and potassium hydride; sodium ethoxide, sodium methoxide and potassium t-butoxide. The amount of these bases to be employed ranges, preferably, from about 1 to about 5 mol. relative to the compound (VIII). The amount of the compound (VIII) to be used ranges from 1 to 5 mol., preferably from 1 to 3 mol., relative to the compound (VII). This reaction is conducted generally at temperatures ranging from −50° C. to 150° C., preferably from about −10° C. to 100° C. The reaction time ranges from 0.5 to 30 hours.

Then, the compound (IX) is subjected to reduction to produce an alcohol derivative (X). This reduction reaction can be conducted by a per se known method, for example, reduction with a metal hydride, reduction with a metal hydride complex, and reduction with diborane and a substituted borane. In other words, this reaction can be conducted by treating the compound (IX) with a reducing agent. Examples of the reducing agent include alkali metal borohydrides (e.g. sodium borohydride and lithium borohydride); metal hydride complex such as lithium aluminum hydride; and diborane, and use of diisobutyl aluminum hydride serves to conduct the reaction advantageously. This reaction is conducted in an organic solvent inert to the reaction. Examples of the solvent include aromatic hydrocarbons such as benzene, toluene and xylene; halogenated hydrocarbons such as chloroform, carbon tetrachloride, dichloromethane, 1,2-dichloroethane and 1,1,2,2-tetrachloroethane; ethers such as diethyl ether, tetrahydrofuran and dioxane; alcohols such as methanol, ethanol, propanol, isopropanol and 2-methoxyethanol; amides such as N,N-dimethylformamide; or a suitable mixture of them, and, from among these solvents, a suitable one is selectively employed depending on kinds of the reducing agent. The reaction temperatures ranges from −20° C. to 150° C., especially preferably from 0° C. to 100° C., and the reaction time ranges from about 1 to 24 hours.

Then, the compound (X) is subjected to oxidation to produce an unsaturated aldehyde derivative (II-1). This oxidation reaction can be conducted by a per se known method, for example, oxidation with manganese dioxide, oxidation with chromic acid, oxidation with dimethyl sulfoxide, or the like. In other words, this reaction is conducted by processing the compound (X) with an oxidizing agent. As the oxidizing agent, use is made of manganese dioxide or chromic anhydride, and use of the former is preferable to conduct the reaction more advantageously. This reaction is conducted in an organic solvent inert to the reaction. As the solvent, use is made of, for example, aromatic hydrocarbons such as benzene, toluene or xylene, halogenated hydrocarbons such as chloroform, carbon tetrachloride, dichloromethane, 1,2-dichloroethane or 1,1,2,2 -tetrachloroethane, ethers such as diethyl ether, tetrahydrofuran or dioxane, dimethyl sulfoxide or a suitable mixture solvent thereof, and, from among these solvents, a suitable one is selectively employed depending of kinds of the oxidizing agent. The reaction temperatures range from −20° C. to 150° C., especially those ranging from OaC to Ioa° C. are preferable, and the reaction time ranges from about 1 to 24 hours.

Then, the compound (II-1) is subjected to reduction reaction to produce the compound (II-2). This reduction reaction is conducted in the same manner as Method C.

The aldehyde derivative (II-1), (II-2) thus obtained can be isolated and purified by means of a conventional refining process, for example, concentration, concentration under reduced pressure, solvent extraction, crystallization, recrystallization, phasic transfer, chromatography or the like.

The compound (VII), which is the starting compound in Method F, can be synthesized in accordance with any method described in, for example, Chemical & Pharmaceutical Bulletin, Vol.39, p.1440 (1990), JPA H4(1992)-225978, JPA S61(1986)-85372, JPA S61(1986)-271287, JPA S63 (1988)-139182, JPA H3(1991)-170478, W09119496-Al, EP-428312-A, JPA H1(1989)-299289 and JPA S63(1988)-230689.

The pyridine aldehyde derivatives (VII-1) can for example be prepared by Method G.

Method G

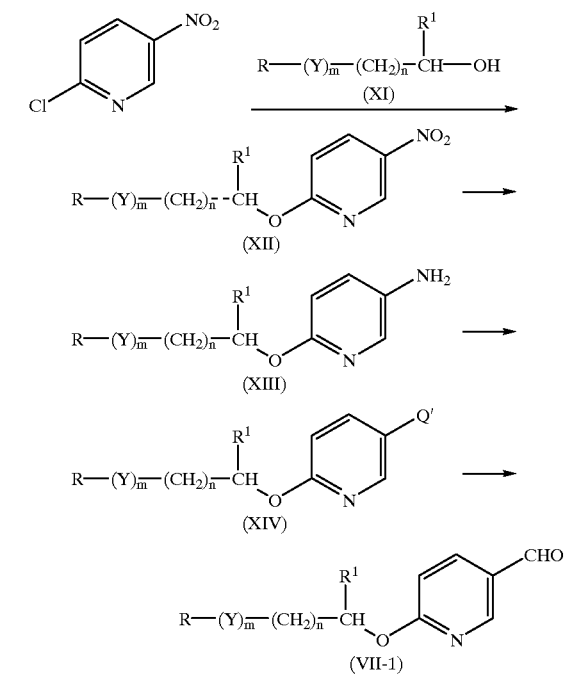

(wherein Q' is a halogen atom, and other symbols have the meaning given above.)

As the halogen atom shown by Q', chlorine, bromine, iodine may be mentioned.

In this method, firstly, 2-chloro-5-nitropyridine is allowed to react with an alcohol derivative to produce the compound (XII). The reaction of 2-chloro-5-nitropyridine with the compound (XI) is conducted in a suitable solvent in the presence of a base in accordance with a conventional method. As the solvent, mention is made of, for example, aromatic hydrocarbons such as benzene, toluene or xylene, ethers such as dioxane, tetrahydrofuran or dimethoxyethane, N,N-dimethylformamide, dimethyl sulfoxide, chloroform, dichloromethane, 1,2-dichloroethane, 1,1,2,2-tetrachloroethane and a suitable mixture solvent of them. As the base, mention is made of, alkali metal salts such as sodium hydroxide, potassium hydroxide, potassium carbonate, sodium carbonate or sodium hydrogencarbonate; amines such as pyridine, triethylamine or N,N-dimethylaniline; metal hydrides such as sodium hydride or potassium hydride; sodium ethoxide, sodium methoxide and potassium t-butoxide. The amount of these bases to be used is preferably in the range from 1 to about 5 mol. relative to the compound (XI). This reaction is conducted usually at temperatures ranging from −50° C. to 150° C., preferable from about −10° C. to 100° C. The reaction time ranges from 0.5 to 30 hours.

Then, the compound (XII) is subjected to reduction to produce an amine derivative (XIII). While the reduction reaction can be conducted by a per se known method, catalytic reduction using a metal catalyst serves to perform the reduction more advantageously. This catalytic reduction is conducted, in accordance with a conventional method, in the presence of a catalyst in hydrogen atmosphere of 1 to 150 atmospheric pressure. Examples of the solvent include alcohols such as methanol, ethanol, propanol, isopropanol and 2-methoxyethanol; aromatic hydrocarbons such as benzene, toluene and xylene; ethers such as ethyl ether, isopropyl ether, dioxane and tetrahydrofuran; halogenated hydrocarbons such as chloroform, dichloromethane and 1,1,2,2-tetrachloroethane; ethyl acetate, acetic acid, N,N-dimethylformamide or a suitable mixture solvent of them. Use of, for example, a metal such as a nickel compound, a transition metal catalyst such as palladium, platinum or rhodium, as the catalyst serves to perform the reaction advantageously. The reaction temperature ranges from 0 to 100° C., preferably from 10 to 80° C., and the reaction time ranges from 0.5 to 50 hours.

Then, the compound (XIII) is subjected to the per se known the Sandmeyer reaction to produce a halogen derivative (XIV). In this reaction, firstly, the compound (XIII) is diazotized by adding dropwise thereto an aqueous solution of sodium nitrite in a solvent in the presence of hydrochloric acid, hydrobromic acid or hydroiodic acid, which was then allowed to react with an aqueous solution of sodium halogenate or potassium halogenate, to thereby produce the compound (XIV). As the solvent, use is made of alcohols such as methanol, ethanol, propanol, isopropanol and 2-methoxyethanol; ethers such as acetone, 2-butanone, dioxane and tetrahydrofuran; or a suitable mixture solvent of them. The reaction temperature ranges from −50° C. to 100° C., preferably from −20 to 60° C. The reaction time ranges from 0.5 to 50 hours.

Then, the compound (XIV) is processed with, for example, butyl lithium, sec.-butyl lithium, tert.-butyl lithium, methyl lithium, phenyl lithium or phenyl magnesium bromide, which is then allowed to react with N,N-dimethylformamide (DMF) to produce a compound (VII-1).

A part of the intermediate compound (IX) in Method F can be produced also by, for example, Method H.

Method H

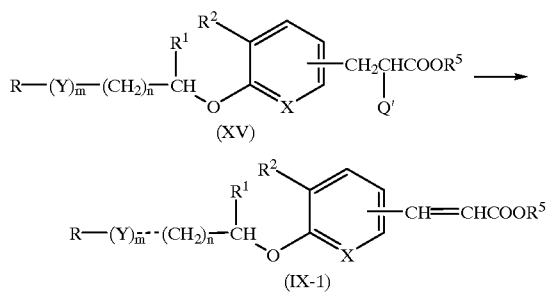

[wherein each symbol is of the same meaning as defined above]

This reaction can be conducted in a suitable solvent in the presence of a base. As the solvent, mention is made of aromatic hydrocarbons such as benzene, toluene and xylene; ethers such as dioxane, tetrahydrofuran and dimethoxyethane; alcohols such as methanol, ethanol and propanol; ethyl acetate, acetonitrile, pyridine, N,N-dimethylformamide, dimethyl sulfoxide, chloroform, dichloromethane, 1,2-dichloroethane, 1,1,2,2-tetrachloroethane, acetone, 2-butanone, and a suitable mixture solvent of them. As the base, mention is made of an inorganic base including, for example, alkali metal hydroxide (e.g. sodium hydroxide and potassium hydroxide), alkaline earth metal hydroxide (e.g. magnesium hydroxide and calcium hydroxide), alkali metal carbonate (e.g. sodium carbonate and potassium carbonate), alkaline earth metal carbonate (e.g. magnesium carbonate and calcium carbonate), alkali metal hydrogencarbonate (e.g. sodium hydrogencarbonate and potassium hydrogencarbonate) and alkali metal acetate (e.g. sodium acetate and potassium acetate); and an organic base including trialkylamine (e.g. trimethylamine and triethylamine), picoline, N-methylpyrrolidine, N-methylmorpholine, 1,5-diazabicyclo[4,3,0]non-5-en, 1,4-diazabicyclo[2,2,2]non-5-ene and 1,8-diazabicyclo[5,4,0]-7-undecene. The amount of these bases to be used ranges preferably from about 1 to about 5 mol. relative to the compound (XV). This reaction is conducted usually at temperatures ranging from −20° C. to 150° C. preferably from about −10° C. to 100° C.

Methods of synthesizing the starting compound (XV) in Method H are described in, for example, Chemical & Pharmaceutical Bulletin, 30, p.3563 (1982), Chemical & Pharmaceutical Bulletin, 30, p.3580 (1982), Chemical & Pharmaceutical Bulletin, 32, p.2267 (1984), Arzneimittel-Forschung/Drug Research 40, p37 (1990), Journal of Medicinal Chemistry, 35 p.2617 (1992), JPA S61(1986)-267580, JPA S61(1986)-286376, JPA S61(1986)-85372, JPA H2(1990)-31079 and JPA S62(1987)-5981.

The compound (III) used in Method B is produced by, for example, Method I.

Method I

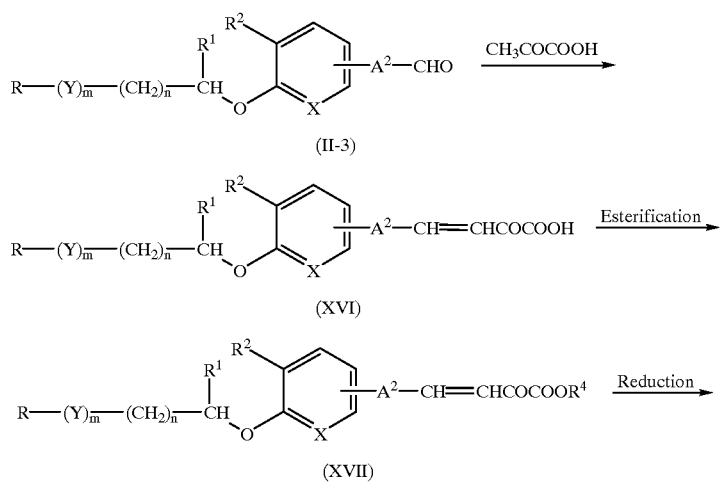

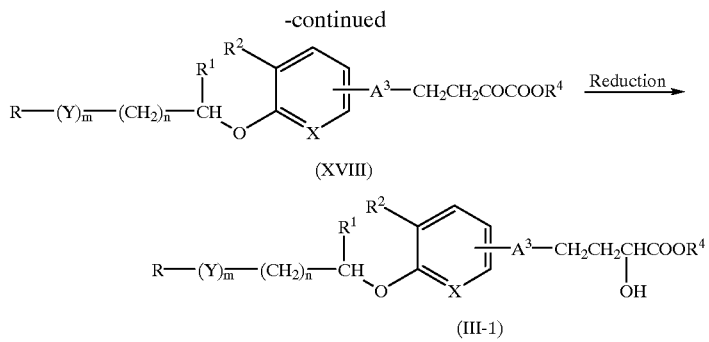

(XVIII)

(III-1)

[wherein $A^2$ is a bond or bivalent straight or branched hydrocarbon chain residue having 1 to 5 carbon atoms; $A^3$ is a bond or a bivalent saturated straight or branched hydrocarbon chain residue having 1 to 5 carbon atoms, and the other symbols is of the same meaning as defined above]

The bivalent straight or branched hydrocarbon chain residue shown by $A^2$ is the one having 1 to 5 carbon atoms among the bivalent straight or branched hydrocarbon chain residue shown by A, and the bivalent saturated straight or branched hydrocarbon residue shown by $A^3$ is the saturated one among the bivalent straight or branched hydrocarbon chain residue shown by $A^2$.

In this method, firstly, the compound (II-3) is condensed with pyruvic acid to produce a compound (XVI). Condensation reaction of the compound (II-3) with pyruvic acid is conducted in a mixture of alcohols and water using the same base as in the reaction of the compound (II) with 2,4-oxazolidinedione in Method A. Then, the compound (XVI) is subjected to esterification to produce a compound (XVII). This esterification reaction can be conducted by a per se known method, for example, a method which comprises allowing the compound (XVII) to react directly with alcohol ($R^4OH$) in the presence of an acid to cause esterification, or a method which comprises a reactive derivative of the compound (XVI), for example, acid anhydride, acid halide (acid chloride, acid bromide), imidazolide or a mixed acid anhydride (e.g. anhydride with methyl carbonate, anhydride with ethyl carbonate, anhydride with isobutyl carbonate or the like) to adequately react with alcohol ($R^4OH$). Then, the compound (XVII) is subjected to catalytic reduction to produce a compound (XVIII). This catalytic reduction is conducted in substantially the same manner as in Method C. Then, the compound (XVIII) is subjected to reduction to produce a compound (III-1). This reduction reaction can be conducted by a per se known method. For example, reduction by using a metal hydride, reduction by using a metal hydride complex compound, reduction by using diborane or a substituted diborane, catalytic hydrogenation or the like are mentioned. In other words, this reaction is conducted by processing the compound (XVIII) with a reducing agent. As the reducing agent, mention is made of alkali metal borohydride (e.g. sodium borohydride, lithium borohydride, etc.), a metal hydride complex compound such as lithium aluminum hydride, metal hydride such as sodium hydride, an organotin compound (triphenyltin hydride, etc.), metals and metal salts including nickel compounds, zinc compounds or the like, transition metal catalysts including palladium, platinum, rhodium or the like, to be used together with hydrogen, and diborane, among others. Above all, use of alkali metal borohydride (e.g. sodium borohydride, lithium borohydride, etc.) is advantageous. This reaction is conducted in an organic solvent which does not give undesirable influences upon the reaction. Examples of the solvent include aromatic hydrocarbons such as benzene, toluene and xylene; halogenated hydrocarbons such as chloroform, carbon tetrachloride, dichloromethane, 1,2-dichloroethane and 1,1,2,2-tetrachloroethane; ethers such as diethyl ether, tetrahydrofuran and dioxane; alcohols such as methanol, ethanol, propanol, isopropanol and 2-methoxyethanol; amides such as N,N-dimethylformamide; or a suitable mixture of these solvents. From among them, a suitable one is selectively employed depending on types of reducing agents. The reaction temperature ranges preferably, from −20° C. to 150° C., especially from 0° C. to 100° C. The reaction time ranges from about 1 to 24 hours.

The starting compound (IV) of Method D and the starting compound (II) of Method A can, for example, be prepared by Method J.

Method J

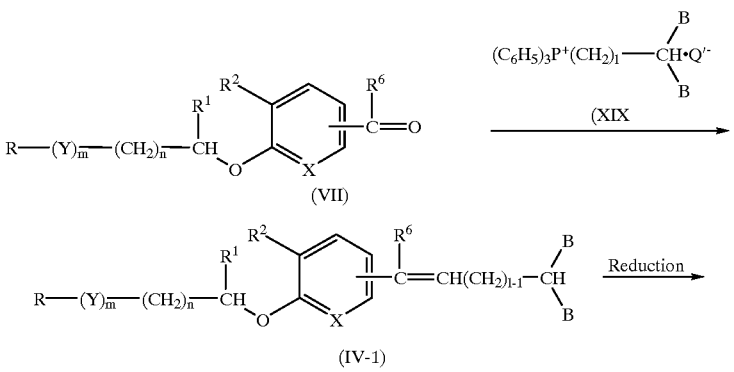

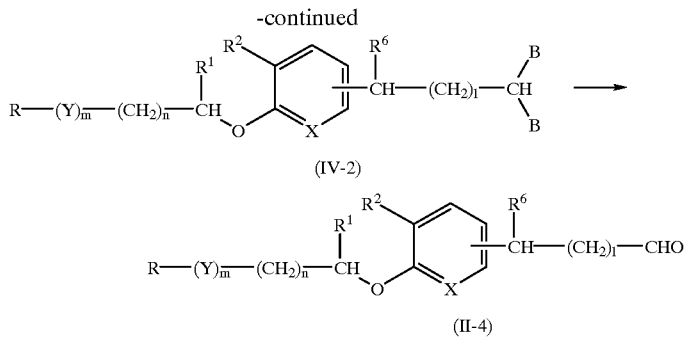

[wherein l is an integer of from 1 to 6, and other symbols have the meaning given above.]

In this method, firstly, the compound (VII) is condensed with the compound (XIX) to produce a compound (IV-1). This condensation reaction is conducted in substantially the same manner as in the reaction of the compound (VII) with the compound (VIII) in Method F. Then, the compound (IV-1) is subjected to reduction reaction to give (IV-2). This reduction reaction is substantially the same manner as in the catalytic reduction reaction of the compound (I-B1) in Method C. The compound (IV-2) can be led to an aldehyde derivative (II-4) by subjecting the former to deprotection by processing with an acid in an aqueous solvent. As the aqueous solvent, mention is made of a mixture of an alcohol such as methanol, ethanol and propanol; an ether such as tetrahydrofuran and dioxane; acetonitrile, acetone, 2-butanone, acetic acid or the like, with water. As the acid, mention is made of, for example, p-toluenesulfonic acid, besides, inorganic acid such as hydrochloric acid, sulfuric acid, nitric acid and hydrobromic acid.

A part of the compounds (II) and (IV) can be prepared by Method K.

Method K

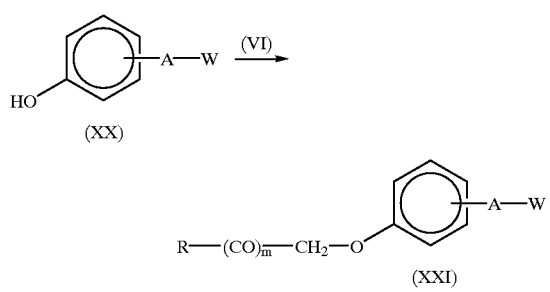

[wherein w is

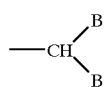

(B has the meaning shown above), and other symbols have the meaning shown above.] This reaction is carried out by a similar manner to that in Method E.

A part of the compound produced by Method E can be subjected to reduction to give a compound (I-B2a2).

Method L

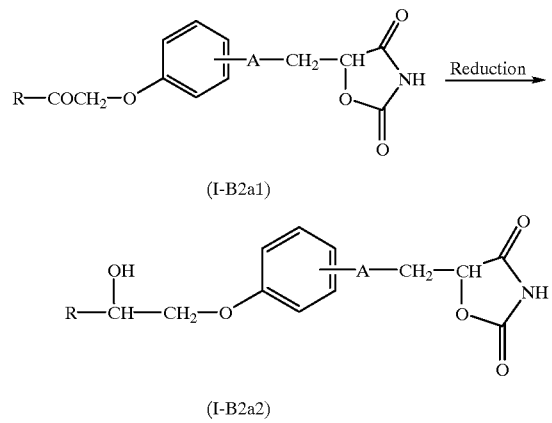

(wherein each symbol has the meaning given above.) This reaction is carried out by a similar manner to that in reduction of Method I in which compound (XVIII) is introduced to compound (III-1).

The compounds (II-2) and (II-4) can also be prepared by Method M.

Method M

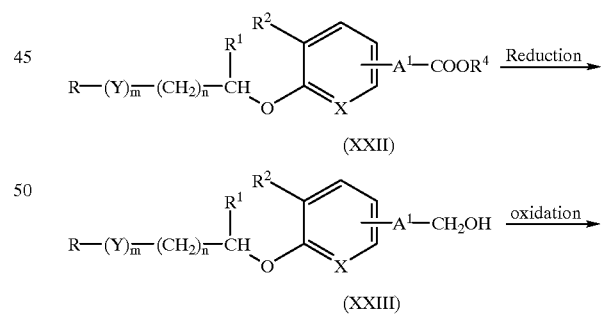

(wherein each symbol has the meaning given above.)

The compound (XXII), which is produced by catalytic hydrogenation of the compound (XI), can be converted to compound (XXIII). The reaction is carried out by a similar manner to that in the reaction of Method F in which compound (IX) is introduced to compound (X). Compound (XXIII) can be subjected to oxidation to give compounds (II-2) and (II-4).

This oxidation reaction is carried out by a known conventional manner such as Jones' oxidation using sulfuric acid-pyridine, Collins oxidation using chromium oxide-pyridine complex, oxidation using pyridinium chlorochromate (PCC), pyridinium dichromate (PDC), oxidation using activated dimethyl sulfoxide (DMSO), oxidation using oxoammonium salt, etc. It is preferable to use activated DMSO when the the starting compound which is subjected to oxidation is optically active. Oxidation using activated DMSO is carried out in the presence of DMSO and an electrophilic reagent in a solvent. As the solvent, mention is made of ethers (e.g. ethyl ether, isopropyl ether, tetrahydrofuran, dioxane, etc.), aromatic hydrocarbons (e.g. benzene, toluene, xylene, etc.), N,N-dimethylformamide (DMF), halogenated hydrocarbons (e.g. chloroform, dichloromethane, etc.), pyridine and dimethyl sulfoxide. From these solvent, a proper solvent can be selected in view of the kind of electrophilic reagent used.

As the oxidation using DMSO, there are dicyclohexylcarbodiimide-method, acetic anhydride-method, phosphorous pentoxide-method, chlorine-method, sulfurtrioxide-pyridine-method, keteneimire-enamine-method, mercury-acetate (II)-method, etc. Among them, sulfur trioxide-pyridine-method is advantageously used. Sulfur trioxide-pyridine-method is carried out by using sulfur trioxide-pyridine complex as an activator for DMSO in the presence of triethylamine. This method can be carried out using an excess amount of DMSO as a solvent. Trilthylamine and sulfur trioxide-pyridine complex each are used in the range of 1 to 10 mol equivalent, preferably 2 to 5 mol equivalent relative to one mole equivalent of compound (XXIII). The reaction temperature is −70° C. to 80° C., preferably −20° C. to 40° C. The reaction time ranges usually from 0.5 to 10 hours.

The aldehyde derivatives (II-2), (II-4) thus obtained can be isolated and purified by means of conventional refining process, for example, concentration, concentration under reduced pressure, solvent extraction, crystallization, recrystallization, phasic transfer, chromatography or the like.

The compounds (II-2) and (II-4) can be converted to compound (IV-2) by acetalization or dithioacetalization.

Among the compound (XXII), benzoxazole derivative (XII-1) can be prepared by Method N.

Method N

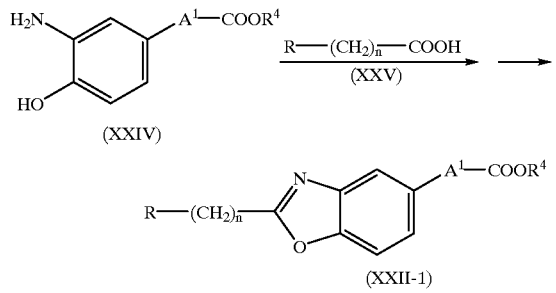

(wherein each symbol has the meaning given above)

This reaction is conducted in an organic solvent inert to the reaction. Examples of the solvent include aromatic hydrocarbons such as xylene, toluene, benzene, etc., ethers such as tetrahydrofuran, dioxane, etc., halogenated hydrocarbons such as dichlorobenzene, chlorobenzene, methylenechloride, etc. While sole solvent may be used, a mixture of two or more solvent may be used.

This reaction is usually carried out by heating a mixture of compound (XXIV) and (XXV) in a suitable solvent. The temperature is usually about 30° C. to about 200° C., preferably about 50° C. to 180° C.

This reaction may be conducted in the presence of a dehydrating agent. As the dehydrating agent, phosphorous compound such as phosphorus pentoxide and phosphorus oxychloride are mentioned. The dehydrating agent is used in an amount of about 1 to 10 mole equivalent, preferably about 1 to 4 mole equivalent relative to the compound (XXIV). When phosphorus oxychloride is used, it can be used in an large excess amount as a solvent. When phosphorus pentoxide is used, addition of hexamethyldisiloxane $\{[CH_3]_3Si]_2O\}$ is advantageous to proceed the reaction. In this case, it is preferable to use hexamethyldisiloxane in an amount of about 2 to 4 mole equivalent relative to phosphorus pentoxide. The reaction time is usually about 1 to 30 hours, preferably about 1 to 10 hours.

The compound (I) of this invention possess excellent hypoglycemic and hypolipidemic activities.

EXPERIMENTAL EXAMPLE

Hypoglycemic and hypolipidemic actions in mice

A test compound mixed in a powdery feed (CE-2, Japan Clea) at a rate of 0.005% was fed to KKA$^y$ mice (9–14 week old) freely for 4 days. During the period, the animals had free access to water. Blood was collected from the orbital venous plexus. Using the plasma, glucose and triglyceride were enzymatically determined quantitatively by using Iatrochem-GLU(A) and Iatro-MA701 TG kit (Iatron Inc.). The respective values are percents reduction (%) found in drug-dosed groups from the control group not receiving the test compound, which are shown in [Table 1].

TABLE 1

| Compound (Example No.) | Hypoglycemic Action % reduction | Hypolipidemic Action % reduction |
| --- | --- | --- |
| 18 | 49 | 41 |
| 19 | 50 | 36 |
| 23 | 39 | 33 |
| 24 | 56 | 53 |
| 26 | 42 | 32 |
| 27 | 53 | 15 |
| 29 | 61 | 83 |
| 30 | 57 | 70 |
| 32 | 63 | 60 |
| 33 | 45 | 59 |
| 34 | 43 | 51 |
| 35 | 42 | 32 |
| 36 | 56 | 48 |
| 43 | 58 | 75 |
| 52 | 54 | 82 |
| 56 | 32 | 24 |
| 60 | 54 | 77 |

As stated above, 2,4-oxazolidinedione derivatives (I) of the present invention exhibit excellent hypoglycemic and hypolipidemic actions, and are pharmaceutically useful as therapeutic agents for diabetes, hyperlipemia and hypertension, for example.

EXAMPLE 1

A mixture of (E)-4-[2-[5-methyl-2-(3-methylphenyl)-4-oxazolyl]ethoxy]cinnamaldehyde (1.20 g), 2,4-oxazolidinedione (0.525 g), piperidine (0.09 g) and ethanol (20 ml) was heated for 5 hours under reflux. The reaction mixture was poured into water, which was acidified with 2N HCl, followed by extraction with ethyl acetate. The ethyl acetate layer was washed with water, dried (MgSO$_4$) and, then, concentrated. The concentrate was purified by means of a silica gel column chromatography. From the fractions eluted with chloroform-methanol (50:1) was obtained 5-[4-

[2-[5-methyl-2-(3-methylphenyl)-4-oxazolyl]ethoxy]cinnamylidene]-2,4-oxazolidinedione (0.51g, 34%). Recrystallization from dichloromethane-methanol gave pale yellow prisms, m.p.213–214° C.

EXAMPLE 2 TO EXAMPLE 7

In substantially the same manner as in Example 1, compounds shown in [Table 2] were obtained.

2-propenylidene]-2,4-oxazolidinedione was obtained. Recrystallization from ethanol-chloroform-isopropyl ether gave pale yellow crystals, m.p.204–205° C.

EXAMPLE 9

A mixture of 2-[3-[4-[2-(5-methyl-2-phenyl-4-oxazolyl)ethoxy]phenyl]propyl]-1,3-dioxane (2.0 g), 2,4-oxazolidinedione (0.99 g), piperidine (0.21 g) and acetic

TABLE 2

R—O—⟨phenyl⟩—CH=CH—CH=⟨(E) 2,4-oxazolidinedione⟩

| Example No. | R | Yield (%) | m.p. (° C.) | Recrystallization solvent |
| --- | --- | --- | --- | --- |
| 2 | $C_2H_5$—⟨pyridyl⟩—$CH_2CH_2$— | 30 | 211–213 (decomposition) | chloroform-methanol |
| 3 | ⟨2-phenyl-5-methyl-oxazol-4-yl⟩—$CH_2CH_2$— | 26 | 227–228 | chloroform-methanol |
| 4 | ⟨2-(2-thienyl)-5-methyl-oxazol-4-yl⟩—$CH_2CH_2$— | 29 | 222–224 | dichloromethane-methanol |
| 5 | ⟨2-(2-furyl)-5-methyl-oxazol-4-yl⟩—$CH_2CH_2$— | 31 | 206–207 | dichloromethane-methanol |
| 6 | ⟨2-phenyl-5-isopropyl-oxazol-4-yl⟩—$CH_2CH_2$— | 23 | Note 1 197–198 | chloroform-methanol-hexane |
| 7 | ⟨2-phenyl-5-methyl-thiazol-4-yl⟩—$CH_2CH_2$— | 23 | 203–204 | ethyl acetate-hexane |

Note 1
½ hydrate

EXAMPLE 8

In substantially the same manner as in Example 1, 5-[3-[2-[2-(5-methyl-2-phenyl-4-oxazolyl)-ethoxy]-5-pyridyl]- acid (50 ml) was heated for 24 hours under reflux. The reaction mixture was concentrated under reduced pressure, to which was added ethyl acetate. The ethyl acetate layer was washed with an aqueous solution of sodium hydrogencarbonate, 2N HCl and water, successively, which was then dried (MgSO$_4$), followed by concentration. The concentrate was purified by means of a silica gel column chromatography. From the fractions eluted with chloroform - ethyl acetate (5:1), 5-[4-[4-[2-(5-methyl-2-phenyl-4-oxazolyl)ethoxy]phenyl]butylidene]-2,4-oxazolidinedione (0.55 g, 26%) was obtained. Recrystallization from ethyl ether-methanol gave colorless needles, m.p.152–153° C.

EXAMPLE 10 TO EXAMPLE 13

In substantially the same manner as in Example 1, compounds shown in [Table 3] were obtained.

pentadien-1-al was allowed to react with 2,4-oxazolidinedione to give 5-[5-[4-[2-(5-methyl-2-phenyl-4-oxazolyl)ethoxy]phenyl]-2,4-pentadienylidene]-2,4-oxazolidinedione. The yield was 31%. Recrystallization from dichloromethane-methanol gave yellow needles, m.p.209–211° C.

EXAMPLE 16

A mixture of 5-[4-[2-[5-methyl-2-(3-methylphenyl)-4-oxazolyl]ethoxy]cinnamylidene]-2,4-oxazolidinedione (0.29 g), palladium-carbon (10%, 0.1 g) and dioxane (50 ml) was subjected to catalytic hydrogenation at room temperature under atmospheric pressure. The catalyst was filtered

TABLE 3

| Example No. | R | Yield (%) | m.p. (° C.) | Recrystallization solvent |
|---|---|---|---|---|
| 10 | 4-methylphenyl-oxazole-CH$_2$CH$_2$— (with CH$_3$ on oxazole) | 33 | 198–200 | dichloromethane methanol |
| 11 | 2-naphthyl-oxazole-CH$_2$CH$_2$— (with CH$_3$ on oxazole) | 31 | 195–197 | dichloromethane methanol |
| 12 | 2-ethyl-oxazole-CH$_2$CH$_2$— (with CH$_3$ on oxazole) | 42 | 201–203 | methanol-ethyl acetate |
| 13 | 2-phenyl-oxazole-CH$_2$— (with CH$_3$ on oxazole) | 26 | 244–245 | chloroform-methanol |

EXAMPLE 14

In substantially the same manner as in Example 1, (E)-3-[2-(5-methyl-2-phenyl-4-oxazolylmethyl)benzofuran-5-yl]acrolein was allowed to react with 2,4-oxazolidinedione to give 5-[3-[2-(5-methyl-2-phenyl-4-oxazolylmethyl)benzofuran-5-yl]-2-propenylidene]-2,4-oxazolidinedione. The yield was 44%. Recrystallization from dichloromethane-methanol gave pale yellow needles, m.p.237–239° C.

EXAMPLE 15

In substantially the same manner as in Example 1, (E,E)-5-[4-[2-(5-methyl-2-phenyl-4-oxazolyl)ethoxy]phenyl]-2,4- off, and the filtrate was concentrated under reduced pressure. The concentrate was purified by means of a silica gel column chromatography. From the fractions eluted with chloroform-methanol (100:3) was obtained 5-[3-[4-[2-[5-methyl-2-(3-methylphenyl)-4-oxazolyl]ethoxy]phenyl]propyl]-2,4-oxazolidinedione (0.28 g, 96%). This product was recrystallized from dichloromethane-methanol to give colorless prisms, m.p.149–150° C.

Elemental Analysis for $C_{25}H_{26}N_2O_5$: Calcd.: C, 69.11; H, 6.03; N, 6.45 Found : C, 69.18; H, 6.01; N, 6.46

EXAMPLE 17 TO EXAMPLE 22

In substantially the same manner as in Example 16, compounds set forth in [Table 4] were obtained.

TABLE 4

R—O—⟨phenyl⟩—CH$_2$CH$_2$CH$_2$—[oxazolidine-2,4-dione]

| Example No. | R 22 | Yield (%) | m.p. (° C.) | Recrystallization solvent |
|---|---|---|---|---|
| 17 | C$_2$H$_5$-pyridyl-CH$_2$CH$_2$— | 87 | 143–144 | dichloromethane-methanol |
| 18 | 2-phenyl-5-methyl-oxazol-4-yl-CH$_2$CH$_2$— | 77 | 162–163 | ethyl acetate-hexane |
| 19 | 2-(2-thienyl)-5-methyl-oxazol-4-yl-CH$_2$CH$_2$— | 57 | 169–170 | dichloromethane-methanol |
| 20 | 2-(2-furyl)-5-methyl-oxazol-4-yl-CH$_2$CH$_2$— | 59 | 153–154 | dichloromethane-methanol |
| 21 | 2-phenyl-5-isopropyl-oxazol-4-yl-CH$_2$CH$_2$— | 34 | 154–155 | ethyl acetate-hexane-isopropyl ether |
| 22 | 2-phenyl-5-methyl-thiazol-4-yl-CH$_2$CH$_2$— | 89 | 127–128 | ethyl acetate-hexane |

EXAMPLE 23

In substantially the same manner as in Example 16, 5-[3-[2-[2-(5-methyl-2-phenyl-4-oxazolyl)ethoxy]-5-pyridyl]-2-propenylidene]-2,4-oxazolidinedione was subjected to catalytic hydrogenation to give 5-[3-[2-[2-(5-methyl-2-phenyl-4-oxazolyl)ethoxy)-5-pyridyl]propyl]-2,4-oxazolidinedione. The product was recrystallized from chloroform-methanol-isopropyl ether to give colorless crystals, m.p.169–171° C.

Elemental Analysis for C$_{23}$H$_{23}$N$_3$O$_5$·1/2H$_2$O: Calcd.: C, 64.18; H, 5.62; N, 9.76 Found: C, 64.31; H, 5.70; N, 9.48

EXAMPLE 24

A mixture of ethyl 2-hydroxy-4-[4-[2-(5-methyl-2-phenyl-4-oxazolyl)ethoxy]phenyl]butyrate (0.45 g), powdery potassium cyanate (0.24 g) and butanol (20 ml) was heated for 4 days under reflux. The solvent was distilled off under reduced pressure, and the residue was acidified with 2N HCl, followed by extraction with ethyl acetate. The ethyl acetate layer was washed with water, dried (MgSO₄), and concentrated. The concentrate was purified by means of a silica gel column chromatography. From the fractions eluted with chloroform-methanol (100:3) was obtained 5-(2-[4-[2-(5-methyl-2-phenyl-4-oxazolyl)ethoxy]phenyl]ethyl]-2,4-oxazolidinedione (0.28 g, 63%). The product was recrystallized from dichloromethane-ethanol to give colorless prisms, m.p.193–194° C.

Elemental Analysis for $C_{23}H_{22}N_2O_5$: Calcd.: C, 67.97; H, 5.46; N, 6.89 Found: C, 67.92; H, 5.61; N, 6.64

EXAMPLE 25

A mixture of 5-[4-[4-[2-(5-methyl-2-phenyl-4-oxazolyl) ethoxy]phenyl]butylidene]-2,4-oxazolidinedione (0.38 g), palladium-carbon (10%, 0.2 g) and tetrahydrofuran (40 ml) was subjected to catalytic hydrogenation at room-temperature and 3 atom. The catalyst was filtered off, and the filtrate was concentrated under reduced pressure. The concentrate was purified by means of a silica gel column chromatography. From the fractions eluted with chloroform-methanol (100:3) was obtained 5-[4-[4-[2-(5-methyl-2-phenyl-4-oxazolyl)ethoxy]phenyl]butyl]-2,4-oxazolidinedione (0.25 g, 65%). This product was recrystallized from dichloromethane-methanol to give colorless prisms, m.p.136–137° C.

EXAMPLE 26 TO EXAMPLE 29

In substantially the same manner as in Example 16, compounds shown in Table 5 were obtained.

TABLE 5

R—O—⟨phenyl⟩—CH₂CH₂CH₂—⟨2,4-oxazolidinedione⟩

| Example No. | R | Yield (%) | m.p. (° C.) | Recrystallization solvent |
|---|---|---|---|---|
| 26 | 4-methylphenyl-oxazole-CH₂CH₂— (2-(4-methylphenyl)-5-methyl-oxazol-4-yl-CH₂CH₂—) | 65 | 168–169 | dichloromethane-methanol |
| 27 | 2-naphthyl-oxazole-CH₂CH₂— (2-(2-naphthyl)-5-methyl-oxazol-4-yl-CH₂CH₂—) | 79 | 163–164 | dichloromethane-methanol |
| 28 | 2-ethyl-5-methyl-oxazol-4-yl-CH₂CH₂— | 73 | 138–139 | dichloromethane-isopropyl ether |
| 29 | 2-phenyl-5-methyl-oxazol-4-yl-CH₂— | 52 | 157–158 | ethyl acetate-hexane |

EXAMPLE 30

In substantially the same manner as in Example 16, was obtained 5-(3-[2-(5-methyl-2-phenyl-4-oxazolylmethyl) benzofuran-5-yl]propyl]-2,4-oxazolidinedione. The yield was 80%. Recrystallization of this product from dichloromethane-methanol gave colorless needles, m.p.184–185° C.

EXAMPLE 31

In substantially the same manner as in Example 16, 5-[ 5-[4-[2-(5-methyl-2-phenyl-4-axazolyl)ethoxy]phenyl)-2,4-pentadienylidene]-2,4-oxazolidinedione was subjected to catalytic hydrogenation to give 5-[5-(4-[2-(5-methyl-2-phenyl-4-oxazolyl)ethoxyjphenyl]pentyl]-2,4-oxazolidinedione. The yield was 77%. Recrystallization from dichloromethane-methanol gave colorless needles, m.p.157–158° C.

EXAMPLE 32

In substantially the same manner as in Example 24, 5-[2-[4-(5-methyl-2-phenyl-4-oxazolylmethoxy)phenyl]ethyl]-2,4-oxazolidinedione was obtained. The yield was 35%. Recrystallization from ethyl acetate-hexane gave colorless prisms, m.p.158–159° C.

EXAMPLE 33

To a solution of 5-[5-(4-hydroxyphenyl)pentyl]-2,4-oxazolidinedione (0.9 g) in N,N-dimethylformamide (DMF) (40 ml) was added sodium hydride (60% in oil, 0.28 g). The mixture was stirred for 15 minutes at room temperature, to which was then added 4-chloromethyl-5-methyl-2-phenyloxazole (0.85 g), and the mixture was stirred for 2 hours at 70° C. The reaction mixture was poured into water, acidified with 2N HCl, and subjected to extraction with ethyl acetate. The ethyl acetate layer was washed with water, dried (MgSO$_4$), and then the solvent was distilled off. The oily residue was subjected to a silica gel column chromatography. From the fractions eluted with ethyl acetate-chloroform (.1:5, v/v) was obtained 5-[5-[4-(5-methyl-2-phenyl-4-oxazolylmethoxy)phenyl]pentyl]-2,4-oxazolidinedione (0.86 g, 58%). Recrystallization from dichloromethane-isopropyl ether gave colorless prisms, m.p.120–121° C.

EXAMPLE 34

In substantially the same manner as in Example 33, was obtained 5-[4-[4-(5-methyl-2-phenyl-4-oxazolylmethoxy)phenyl]butyl]-2,4-oxazolidinedione. The yield was 32%. Recrystallization from dichloromethane-isopropyl ether gave colorless prisms, m.p.186–187° C.

EXAMPLE 35

A mixture of 4-[4-[2-(1,3-dioxolan-2-yl)ethyl]phenoxyacetyl]-5-methyl-2-phenyloxazole (1.8 g), 2,4-oxazolidinedione (0.925 g), piperidine (0.12 g) and acetic acid (30 ml) was heated for 15 hours under reflux. The reaction mixture was concentrated under reduced pressure. To the concentrate was added a saturated aqueous solution of sodium hydrogencarbonate, followed by extraction with chloroform. The chloroform layer was washed with water, dried (MgSO$_4$), followed by distilling off the solvent. The oily residue was subjected to a silica gel column chromatography. From the fractions eluted with methanol-chloroform (1:30, v/v) was obtained 5-[3-[4-[2-(5-methyl-2-phenyl-4-oxazolyl)-2-oxoethoxy]phenyl]propylidene]-2,4-oxazolidinedione. This compound was dissolved in tetrahydrofuran (THF) (30 ml), to which was added palladium-carbon (5%, 0.3 g). The mixture was subjected to catalytic hydrogenation. The catalyst was filtered off, and the filtrate was concentrated under reduced pressure. The oily residue was subjected to a silica gel column chromatography. From the fractions eluted with ethyl acetate-hexane (1:1, v/v), 5-[3-[4-[2-(5-methyl-2-phenyl-4-oxazolyl)-2-oxoethoxyaphenyl]propyl]-2,4-oxazolidinedione (0.32 g, 16%) was obtained as an oily product.

NMR (δ ppm in CDCl$_3$): 1.7–2.1(4H,m), 2.63(2H,t,J=7 Hz), 2.74(3H,s), 4.84(1H,dd,J=7&4.5 Hz), 5.37(2H,s), 6.92 (2H,d,J=9 Hz), 7.09(2H,d,J=9 Hz), 7.45–7.55(3H,m), 7.95–8.1(3H,m).

EXAMPLE 36

To a solution of 5-[3-(4-[2-(5-methyl-2-phenyl-4-oxazolyl)-2-oxoethoxyjphenyl]propyl]-2,4-oxazolidinedione (0.2 g) in tetrahydrofuran (THF) (5 ml)-ethanol (5 ml) was added sodium borohydride (0.03 g). The mixture was stirred for one hour at room temperature. To the reaction mixture were added 2N HCl and water, followed by extraction with ethyl acetate. The ethyl acetate layer was washed with water and dried (MgSO$_4$), then the solvent was distilled off. The oily residue was subjected to a silica gel column chromatography. From the reactions eluted with chloroform-methanol (50:1, v/v) was obtained 5-[3-[4-[2-hydroxy-2-(5-methyl-2-phenyl-4-oxazolyl)ethoxy]-phenyl]propyl]-2,4-oxazolidinedione (0.16 g, 80%). Recrystallization from dichloromethane-isopropyl ether gave colorless needles, m.p.146–147° C.

EXAMPLE 37–EXAMPLE 50

In substantially the same manner in Example 33, compounds shown in Table 6 were obtained.

TABLE 6

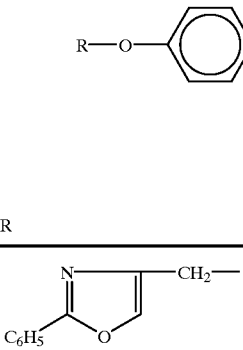

| Example No. | R | k | Yield (%) | m.p. (° C.) | Recrystallization solvent |
|---|---|---|---|---|---|
| 37 | 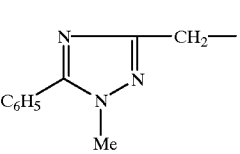 | 3 | 72 | 167–168 | dichloromethane-methanol |
| 38 | | 3 | 66 | 148–149 | dichloromethane isopropyl ether |

TABLE 6-continued $$R-O-C_6H_4-(CH_2)_k-\text{oxazolidinone}$$

| Example No. | R | k | Yield (%) | m.p. (°C.) | Recrystallization solvent |
|---|---|---|---|---|---|
| 39 | 2-C$_6$H$_5$-5-Me-thiazol-4-yl-CH$_2$— | 3 | 71 | 104–105 | dichloromethane isopropyl ether |
| 40 | quinolin-2-yl-CH$_2$— | 3 | 23 | 177–178 | dichloromethane-methanol |
| 41 | pyridin-2-yl-CH$_2$— | 3 | 77 | 196–197 | dichloromethane-methanol |
| 42 | 4-C$_6$H$_5$-5-Me-thiazol-2-yl-CH$_2$— | 3 | 75 | 137–138 | dichloromethane-methanol |
| 43 | 4-C$_6$H$_5$-5-Me-oxazol-2-yl-CH$_2$— | 3 | 81 | 121–122 | dichloromethane-methanol |
| 44 | 2-[(E)-C$_6$H$_5$CH=CH]-oxazol-4-yl-CH$_2$— | 3 | 80 | 155–156 | dichloromethane-methanol |
| 45 | 2-(2-naph)-5-Me-oxazol-4-yl-CH$_2$— | 3 | 84 | 151–152 | dichloromethane-methanol |
| 46 | 2-(1-naph)-5-Me-oxazol-4-yl-CH$_2$— | 3 | 72 | oily product[1] | — |
| 47 | 2-(2-naph)-5-Me-oxazol-4-yl-CH$_2$— | 5 | 79 | 159–160 | dichloromethane-methanol |
| 48 | 2-(furan-2-yl)-5-Me-oxazol-4-yl-CH$_2$— | 3 | 74 | 146–147 | dichloromethane-isopropyl ether |
| 49 | 2-(4-Cl-C$_6$H$_4$)-5-Me-oxazol-4-yl-CH$_2$— | 3 | 70 | 148–149 | dichloromethane-methanol |

TABLE 6-continued

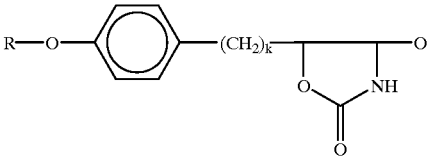

| Example No. | R | k | Yield (%) | m.p. (° C.) | Recrystallization solvent |
| --- | --- | --- | --- | --- | --- |
| 50 | (3,5-bis(CF₃)phenyl-oxazol-CH₂-Me) | 3 | 64 | 184–185 | dichloromethane isopropyl ether |

Note
[1]NMR(δ ppm in CDCl₃): 1.7–2.1(4H, m), 2.59(3H, s), 2.62(2H, t, J=7Hz), 4.79(1H, dd, J=6.5&4.5Hz), 5.07(2H, s), 6.99(2H, d, J=8.5Hz), 7.10(2H, d, J=8.5Hz), 7.45–7.7(3H, m), 7.85–8.0 (2H, m), 8.15(1H, dd, J=7&1Hz), 9.21(1H, d, J=8.5Hz).
Mc: methyl, 2-naph.: 2-naphthyl, 1-naph.: 1-naphthyl

EXAMPLE 51

A mixture of 4-[2-[N-methyl-N-(2-pyridyl)amino]ethoxy]cinnamaldehyde (4.00 g), 2,4-oxazolidinedione (2.86 g), piperidine (0.60 g) and ethanol (50 ml) was heated for 2 hours under reflux. The reaction mixture was concentrated and the residue was subjected to silica gel column chromatography.

Fractions eluted with ethyl acetate-chloroform (1:4) gave crystals. The crystals were dissolved in tetrahydrofuran (100 ml). To the solution was added palldium-carbon (5%, 1.40 g). The mixture was subjected to catalytic hydrogenation at room temperature under atmospheric pressure. The catalyst was filtered off, and the filtrate was concentrated under reduced pressure. The residue was subjected to silica gel column chromatography. From the fractions eluted with chloroform-methanol (100:2), 5-[3-[4-(2-[N-methyl-N-(2-pyridyl)amino]ethoxy]phenyl]propyl]-2,4-oxazolidinedione (1.10 g, 21%) was obtained. Recrystallization from dichloromethane-isopropylether gave colorless prisms. Melting point: 126–127° C.

EXAMPLE 52

In substantially the same manner as in Example 51, 5-[3-[2-(5-methyl-2-phenyl-4-oxazolylmethoxy)-5-pyridyl] propyl]-2,4-oxazolidinedione was obtained as an oily substance. Yield: 22%.

NMR (δ ppm in CDCl₃): 1.7–2.15(4H,m), 2.48(3H,s), 2.61(2H,t,J=7 Hz), 4.84(1H,dd,J=6.5&4.5 Hz), 5.27(2H,s), 6.76(1H,d,J=8.5 Hz), 7.3–7.5(4H,m), 7.95–8.1(3H,m), 8.84 (1H,br s).

EXAMPLE 53

In substantially the same manner as in Example 35, 5-[4-[4-[5-methyl-2-(2-naphthyl)-4-oxazolylmethoxy]phenyl]butyl]-2,4-oxazolidinedione was obtained. Yield: 22%. Recrystallization from dichloromethane-methanol gave colorless prisms. Melting point: 163–164° C.

EXAMPLE 54

In substantially the same manner as in Example 35, 5-[3-[2-(2-naphthylmethyl)benzoxazol-5-yl]propyl]-2,4-oxazolidinedione was obtained. Yield: 13%. Recrystallization from dichloromethane-methanol gave colorless prisms. Melting point: 151-152° C.

Example 55

In substantially the same manner as in Example 1, 5-[3-[3-(5-methyl-2-phenyl-4-oxazolylmethoxy)phenyl]-2-propenylidene]-2,4-oxazolidinedione was obtained. Recrystallization from chloroform-methanol gave colorless needles. Melting point: 229–230° C.

EXAMPLE 56

In substantially the same manner as in Example 16, 5-[3-[3-(5-methyl-2-phenyl-4-oxazolylmethoxy)phenyl]propyl]-2,4-oxazolidinedione was obtained. Recrystallization from ethyl acetate-hexane gave colorless needles. Melting point: 134–135° C.

EXAMPLE 57

In substantially the same manner as in Example 51, 5-[3-(4-isopropoxyphenyl)propyl]-2,4-oxazolidinedione was obtained as an oily substance.

NMR (δ ppm in CDCl₃): 1.32(6H,d,J=6 Hz), 1.65–2.15 (4H,m), 2.62(2H,t,J=7 Hz), 4.4–4.6(1H,m), 4.84(1H,dd,J= 7&4.5 Hz), 6.81(2H,d,J=8.5 Hz), 7.06(2H,d,J=8.5 Hz), 8.00 (1H,broad s).

EXAMPLE 58

In substantially the same manner as in Example 51, 5-[5-(4-isopropoxyphenyl)pentyl]-2,4-oxazolidinedione was obtained as an oily substance.

NMR (δ ppm in CDCl₃): 1.32(6H,d,J=6 Hz), 1.3–2.1(8H, m), 2.54(2H,t,J=7.5 Hz), 4.4–4.6(1H,m), 4.84(1H,dd,J= 7.5&4.5 Hz), 6.80(2H,d,J=8.5 Hz), 7.05(2H,d,J=8.5 Hz), 7.98(1H,broad s).

EXAMPLE 59

In substantially the same manner as in Example 35, 5-[4-(4-isopropoxyphenyl)butyl]-2,4-oxazolidinedione was obtained by reacting 2-[3-(4-isopropoxyphenyl)-propyl]-1,3-dioxolane with 2,4-oxazolidinedione, followed by allowing the reaction product to catalytic hydrogenation. Recrystallization from dichloromethane-isopropylether gave colorless prisms. Melting point: 81–82° C.

EXAMPLE 60

In substantially the same manner as in Example 51, 5-[3-[4-(5-methyl-2-phenyl-4-oxazolylmethoxy)phenyl]-butyl]-2,4-oxazolidinedione was obtained as pale yellow amorphous powder.

NMR(δ ppm in CDCl$_3$): 1.25(3H,d,J=6.8 Hz), 1.30–2.00 (4H,m), 2.43(3H,s), 2.55–2.80(1H,m), 4.67–4.83(1H,m), 4.97(2H,s), 6.95(2H,d,J=8.8 Hz), 7.09(2H,d,J=8.8 Hz), 7.35–7.53(3H,m), 7.92–8.10(2H,m).

EXAMPLE 61

In substantially the same manner as in Example 33, 5-[3-[4-[2-(2-benzo[b]thienyl)-5-methyl-4-oxazolylmethoxy]phenyl]propyl]-2,4-oxazolidinedione was obtained. The yield was 76%. Recrystallization from dichloromethane-isopropyl ether gave colorless prisms, m.p. 154–155° C.

EXAMPLE 62

In substantially the same manner as in Example 33, 5-[3-[4-[2-(2-benzo[b]furanyl)-5-methyl-4-oxazolylmethoxy]phenyl]propyl]-2,4-oxazolidinedione was obtained. The yield was 70%. Recrystallization from dichloromethane-isopropyl ether gave colorless needles, m.p. 165–166° C.

FORMULATION EXAMPLE 1

(Preparation of tablets)

| | |
|---|---:|
| (1) 5-[3-[2-[2-(5-methyl-2-phenyl-4-oxazolyl)ethoxy]-5-pyridyl]propyl]-2,4-oxazolidinedione | 10 g |
| (2) lactose | 50 g |
| (3) corn starch | 15 g |
| (4) carboxymethylcellulose calcium | 44 g |
| (5) magnesium stearate | 1 g |
| 1000 tablets | 120 g |

The whole amounts of above (1), (2) and (3), and 30 g of (4) were kneaded with water, which was subjected to vacuum drying, followed by granulation. Thus-granulated powder was mixed with 14 g of (4) and 1 g of (5), followed by tableting using a tableting machine to prepare 1000 tablets containing 10 mg of (1) per tablet.

FORMULATION EXAMPLE 2

(Preparation of tablets)

| | |
|---|---:|
| (1) 5-[2-[4-[2-(5-methyl-2-phenyl-4-oxazolyl]-ethoxy]phenyl]ethyl]-2,4-oxazolidinedione | 30 g |
| (2) lactose | 50 g |
| (3) corn starch | 15 g |
| (4) carboxymethylcellulose calcium | 44 g |
| (5) magnesium stearate | 1 g |
| 1000 tablets | 140 g |

The whole amounts of above (1), (2) and (3), and 30 g of (4) were kneaded with water, which was subjected to vacuum drying, followed by granulation. Thus-granulated powder was mixed with 14 g of (4) and 1 g of (5), which was tableted by using a tableting machine to prepare 1000 tablets containing 30 mg of (1) per tablet.

REFERENCE EXAMPLE 1

To a solution of triethyl phosphonoacetate (1.79 g) in N,N-dimethylformamide (40 ml) was added, little by little at 0° C., sodium hydride (60% in oil, 0.32 g). The mixture was stirred for 15 minutes at the same temperature. To the reaction mixture was added 4-[2-[5-methyl-2-(3-methylphenyl)-4-oxazolyl]ethoxy]benzaldehyde (2.44 g), and the mixture was stirred for one hour at room temperature. The reaction mixture was poured into ice-water, which was acidified with 2N HCl, and resulting crystalline precipitate was collected by filtration. Recrystallization from ethyl acetate-hexane gave ethyl (E)-4-[2-[5-methyl-2-(3-methylphenyl)-4-oxazolyl]ethoxy]cinnamate (2.52 g, 85%) as colorless needles, m.p.90–91° C.

REFERENCE EXAMPLE 2 TO REFERENCE EXAMPLE 6

In substantially the same manner as in Reference Example 1, compounds shown in [Table 7] were obtained.

TABLE 7

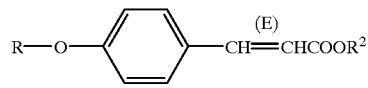

| Reference Example No. | R | R$^2$ | Yield (%) | m.p. (° C.) | Recrystallization solvent |
|---|---|---|---|---|---|
| 2 | 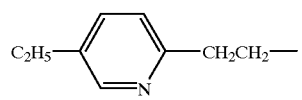 | CH$_3$ | 83 | 84–85 | ethyl ether-hexane |

TABLE 7-continued

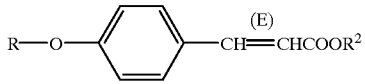

| Reference Example No. | R | R² | Yield (%) | m.p. (° C.) | Recrystallization solvent |
|---|---|---|---|---|---|
| 3 | 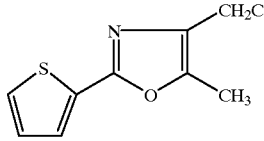CH₂CH₂— | C₂H₅ | 90 | 77–78 | ethyl ether-hexane |
| 4 | 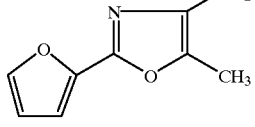CH₂CH₂— | C₂H₅ | 88 | 81–82 | ethyl ether-hexane |
| 5 | 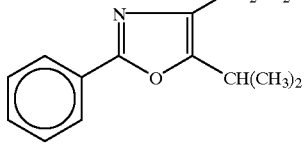CH₂CH₂— | C₂H₅ | 95 | 69–70 | hexane |
| 6 | 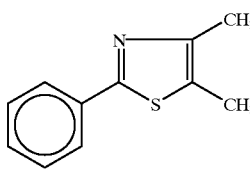CH₂CH₂— | C₂H₅ | 96 | 121–122 | ethyl acetate-hexane |

REFERENCE EXAMPLE 7

A toluene solution of diisobutylaluminum hydride (1.5M, 9.3 ml) was added dropwise at 0° C. to a suspension of ethyl (E)-4-[2-[5-methyl-2-(3-methylphenyl)-4-oxazolyl]ethoxy] cinnamate (2.48 g) in dichloromethane (50 ml). The mixture was stirred for 2 hours at room temperature, to which were then added, under ice-cooling, methanol (3 ml) and, then, water (30 ml). The mixture was subjected to filtration through a celite layer. The organic layer was washed with water, dried (MgSO₄) and, then, concentrated. The concentrate was purified by means of a column chromatography. From the fractions eluted with ethyl acetate-hexane (1:1) was obtained (E)-3-[4-[2-[5-methyl-2-(3-methylphenyl)-4-oxazolyl]ethoxy]phenyl]-2-propen-1-ol (1.44 g, 65%). Recrystallization from dichloromethane-isopropyl ether gave colorless prisms, m.p.116–117° C.

REFERENCE EXAMPLE 8 TO REFERENCE EXAMPLE 13

In substantially the same manner as in Reference Example 7, compounds shown in [Table 8] were obtained.

TABLE 8

$$\text{R—O—} \underset{}{\bigcirc} \text{—CH} \overset{(E)}{=} \text{CHCH}_2\text{OH}$$

| Reference Example No. | R | Yield (%) | m.p. (° C.) | Recrystallization solvent |
|---|---|---|---|---|
| 8 | 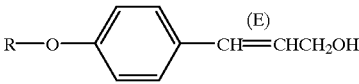 | 81 | Note 1 oily product | — |
| 9 | 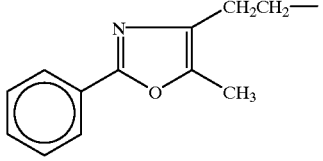 | 90 | 127–128 | ethyl acetate |
| 10 | 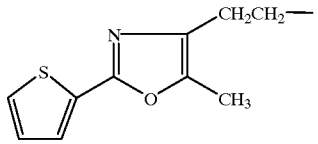 | 68 | 124–125 | dichloromethane-isopropyl ether |
| 11 | 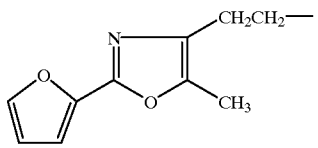 | 81 | 113–114 | dichloromethane-isopropyl ether |
| 12 | 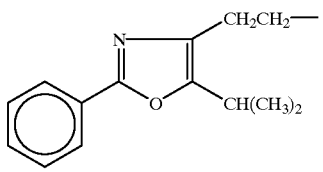 | 29 | 110–111 | ethyl acetate-hexane |
| 13 | 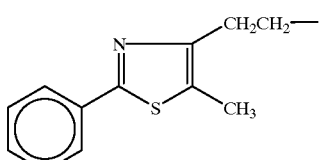 | 85 | 139–140 | ethyl acetate |

Note 1
NMR(δ ppm in CDCl$_3$): 1.24(3H, t, J=7.5Hz), 2.63(2H, q, J=7.5Hz), 3.23(2H, t, J=7Hz), 4.25–4.4(4H, m), 6.23(1H, dt, J=16&6Hz), 6.55(1H, d, J=16Hz), 6.86(2H, d, J=9Hz), 7.19(1H, d, J=8Hz), 7.30(2H, d, J=9Hz), 7.46(1H, dd, J=8&2Hz), 8.40(1H, d, J=2Hz).

REFERENCE EXAMPLE 14

Activated manganese dioxide (2.8 g) was added to a solution of (E)-3-[4-[2-[5-methyl-2-(3-methylphenyl)-4-oxazolyl]ethoxy]phenyl]-2-propen-1-ol (1.4 g) in dichloromethane (50 ml). The mixture was stirred for 2 hours at room temperature, which was subjected to filtration through celite. The filtrate was concentrated to give (E)-4-[2-[5-methyl-2-(3-methylphenyl)-4-oxazolyl]ethoxy] cinnamaldehyde (1.27 g, 91%). Recrystallization from dichloromethane-isopropyl ether gave colorless needles, m.p.110–111° C.

REFERENCE EXAMPLE 15 TO REFERENCE EXAMPLE 20

In substantially the same manner as in Reference Example 14, compounds shown in [Table 9] were obtained.

TABLE 9

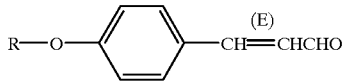

| Reference Example No. | R | Yield (%) | m.p. (° C.) | Recrystallization solvent |
|---|---|---|---|---|
| 15 | 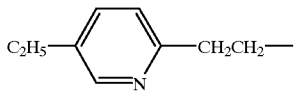 | 84 | 50–51 | ethyl ether-hexane |
| 16 | 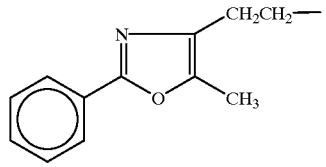 | 94 | 128–129 | ethyl acetate-hexane |
| 17 | 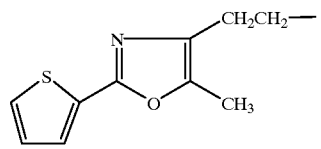 | 97 | 120–121 | dichloromethane-isopropyl ether |
| 18 | 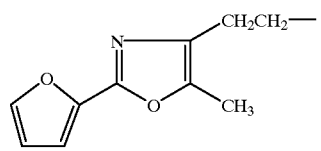 | 93 | 103–104 | dichloromethane-isopropyl ether |
| 19 | 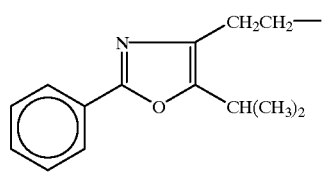 | 93 | 133–134 | ethyl acetate-ethyl ether |
| 20 | 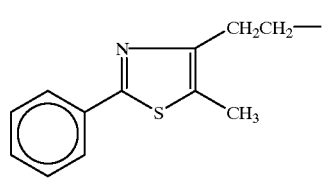 | 88 | 128–129 | ethyl acetate-hexane |

REFERENCE EXAMPLE 21

To a solution of 4-[2-(5-methyl-2-phenyl-4-oxazolyl)ethoxy]benzaldehyde (3.0 g) and pyruvic acid (3.44 g) in methanol (80 ml) was added dropwise a solution of sodium carbonate (4.14 g) in water (80 ml). The mixture was stirred for 24 hours at temperatures ranging from 70 to 80° C., which was poured into water, followed by washing with ethyl acetate. The aqueous layer was acidified with conc. HCl, then resulting crystalline prepcipitate was collected by filtration. The crystals were added to ethanol containing hydrogen chloride (5%, 15 ml), and the mixture was heated for 30 minutes under reflux. The solvent was distilled off under reduced pressure. The residue was dissolved in chloroform. The solution was washed with water, dried (MgSO$_4$) and, then, concentrated. The concentrate was purified by means of a silica gel column chromatography. From the fractions eluted with ethyl acetate - chloroform (1:9) was obtained ethyl (E)-4-[2-(5-methyl-2-phenyl-4-oxazolyl)ethoxy]benzylidene pyruvate (1.0 g, 25%). Recrystallization from dichloromethane-ethanol gave pale yellow needles, m.p.99–100° C.

REFERENCE EXAMPLE 22

A mixture of ethyl (E)-4-[2-(5-methyl-2-phenyl-4-oxazolyl)ethoxy]benzylidene pyruvate (0.85 g), palladium-carbon (10%, 0.1 g) and dioxane (80 ml) was subjected to catalytic hydrogenation at room temperature under atmospheric pressure. The catalyst was filtered off. The filtrate was concentrated under reduced pressure. The concentrate was dissolved in ethanol (20 ml). To the solution was added, under ice-cooling, sodium borohydride (0.08 g), and the mixture was stirred for one hour at room temperature. The reaction mixture was poured into water and neutralized with 1N HCl, followed by extraction with ethyl acetate. The ethyl acetate layer was washed with water, dried (MgSO$_4$) and, then concentrated. The concentrate was purified by means of a silica gel column chromatography. From the fractions eluted with chloroform-ethyl acetate (9:1) was obtained ethyl 2-hydroxy-4-[4-[2-(5-methyl-2-phenyl-4-oxazolyl) ethoxy]phenyl]butyrate (0.55 g, 64%). Recrystallization from ethyl ether - hexane gave colorless needles, m.p.67–68° C.

REFERENCE EXAMPLE 23

To a stirred solution of 2-chloro-5-nitropyridine (25 g), 2-(5-methyl-2-phenyl-4-oxazolyl)ethanol (32.1 g) in THF (250 ml) was added portionwise, under ice-cooling, sodium hydride (60% in oil, 6.92 g). The reaction mixture was stirred for further 15 hours at room temperature, which was poured into water, followed by extraction with ethyl acetate. The ethyl acetate was washed with water and dried (MgSO$_4$), then the solvent was distilled off under reduced pressure. The residual crystals were collected by filtration. Recrystallization from ethanol gave 2-[2-(5-methyl-2-phenyl-4-oxazolyl)ethoxy]-5-nitropyridine (25.4 g, 49%) as yellowish brown crystals, m.p.110.5–111.5° C.

Elemental Analysis for $C_{17}H_{15}N_3O_4$: Calcd.: C, 62.76; H, 4.65; N, 12.92 Found: C, 62.80; H, 4.58; N, 12.96

REFERENCE EXAMPLE 24

A mixture of 2-[2-(5-methyl-2-phenyl-4-oxazolyl) ethoxy]-5-nitropyridine (13.4 g), palladium-carbon (5%, 1.5 g) and ethyl acetate (200 ml)-methanol (150 ml) was subjected catalytic hydrogenation at room temperature under one atmospheric pressure. The catalyst was filtered off, and the filtrate was concentrated under reduced pressure. The residual crystals were collected by filtration to obtain 5-amino-2-[2-(5-methyl-2-phenyl-4-oxazolyl)ethoxy] pyridine (11.4 g, 93%). Recrystallization from ethyl acetate-hexane gave brown crystals, m.p.107.0–108.0° C.

Elemental Analysis for $C_{17}H_{17}N_3O_2$: Calcd.: C, 69.14; H, 5.80; N, 14.23 Found: C, 69.01; H, 5.94; N, 13.99

REFERENCE EXAMPLE 25

To a mixture of 5-amino-2-[2-(5-methyl-2-phenyl-4-oxazolyl)ethoxy]pyridine (10.0 g), conc. HCl (8.47 ml) and acetone (100 ml) was added dropwise a solution of sodium nitrite (NaNO$_2$) (2.46 g) in water (10 ml) at temperatures below 10° C. The mixture was stirred for 30 minutes at 10° C., to which was dropwise added a solution of potassium iodide (KI) (2.46 g) in water (10 ml) at 10° C. The reaction mixture was stirred for further one hour at temperatures raging from 30 to 35° C. and for another one hour at temperatures ranging from 35 to 40° C., followed by concentration under reduced pressure. The concentrate was poured into water, which was subjected to extraction with ethyl acetate. The ethyl acetate layer was washed with water and dried (MgSO$_4$), then the solvent was distilled off under reduced pressure. The residual oily product was subjected to a silica gel chromatography. From the fractions eluted with ethyl acetate-hexane (1:3, v/v) was obtained 5-iodo-2-[2-(5-methyl-2-phenyl-4-oxazolyl)ethoxy]pyridine (7.22 g, 52%). Recrystallization from ethyl acetate-hexane gave colorless crystals, m.p.105–106° C.

Elemental Analysis for $C_{17}H_{15}N_2O_2I$: Calcd.: C, 50.26; H, 3.72; N, 6.90 Found: C, 50.22; HI 3.89; N, 6.78

REFERENCE EXAMPLE 26

To a solution of 5-iodo-2-[2-(5-methyl-2-phenyl-4-oxazolyl)ethoxy]pyridine (2.5 g) in tetrahydrofuran (40 ml) was added dropwise, at −65° C. under nitrogen streams, a hexane solution of n-butyllithium (1.6M, 4.61 ml). The mixture was stirred for 15 minutes at the same temperature, to which was added dropwise N,N-dimethylformamide (0.71 ml). The cooling bath was removed, then the reaction mixture was stirred for further 30 minutes, to which was added a saturated aqueous solution of ammonium chloride (6 ml). The reaction mixture was poured into water, followed by extraction with ethyl acetate. The ethyl acetate was washed with water and dried (MgSO$_4$), then the solvent was distilled off under reduced pressure to leave 5-formyl-2-[2-(5-methyl-2-phenyl-4-oxazolyl)ethoxy]pyridine (1.5 g, 79%). Recrystallization from ethyl acetate-hexane gave colorless crystals, m.p.99–100° C.

Elemental Analysis for $C_{18}H_{16}N_2O_3$: Calcd.: C, 70.12; H, 5.23; N, 9.09 Found: C, 69.94; H, 5.38; N, 8.94

REFERENCE EXAMPLE 27

In substantially the same manner as in Reference Example 1, was obtained methyl 3-[2-[2-(5-methyl-2-phenyl-4-oxazolyl]ethoxy]-5-pyridyl]acrylate. Recrystallization from ethyl acetate gave colorless crystals, m.p.138–139° C.

REFERENCE EXAMPLE 28

In substantially the same manner as in Reference Example 7, (E)-3-[2-[2-(5-methyl-2-phenyl-4-oxazolyl)-ethoxy]-5-pyridyl]-2-propen-1-ol was obtained. Recrystallization from ethyl acetate-isopropyl ether gave colorless crystals, m.p.115–116° C.

REFERENCE EXAMPLE 29

In substantially the same manner as in Reference Example 14, (E)-3-[2-[2-(5-methyl-2-phenyl-4-oxazolyl)-ethoxy]-5-pyridyl]acrolein. Recrystallization from ethyl acetate-hexane gave colorless crystals, m.p.138–139° C.

REFERENCE EXAMPLE 30

A mixture of methyl 2-bromo-3-[4-[2-(5-methyl-2-phenyl-4-oxazolyl)ethoxy]phenyl]propionate (15.0 g), 1,8-diazabicyclo[5,4,0]-7-undecene (DBU) (6.2 g) and toluene (200 ml) was stirred for 2 hours at 70° C. The reaction mixture was poured into ethyl acetate (200 ml), which was washed with 2N HCl and a saturated aqueous saline solution, followed by drying (MgSO$_4$). The solvent was distilled off under reduced pressure to leave methyl 4-[2-(5-methyl-2-phenyl-4-oxazolyl)ethoxy]cinnamate (10.8 g, 88%). Recrystallization from ethyl acetate-hexane colorless needles, m.p.114–115° C.

REFERENCE EXAMPLE 31

Sodium hydride (60% in oil, 0.78 g) was added in limited amounts, at room temperature, to a solution of [2-(1,3-dioxan-2-yl)ethyl]triphenylphosphonium bromide (8.9 g) in N,N-dimethylformamide (100 ml). The mixture was stirred for 30 minutes at the same temperature range, to which was added 4-[2-(5-methyl-2-phenyl-4-oxazolyl)ethoxy]

benzaldehyde (5.0 g). The mixture was stirred for 15 minutes at room temperature, then for 5 hours at 70° C. The reaction mixture was poured into ice-water, which was acidified with 2N $HC_1$, followed by extraction with ethyl acetate. The ethyl acetate layer was washed with water and dried ($MgSO_4$). The residue was purified by means of a silica gel column chromatography. From the fractions eluted with hexane - ethyl acetate (3:1), (Z)-2-[3-[4-[2-(5-methyl-2-phenyl-4-oxazolyl)ethoxy]phenyl]-2-propenyl]-1,3-dioxane (5.1 g, 77%) was obtained as an oily product.

NMR (δ ppm in $CDCl_3$): 1.25–1.4(1H,m), 1.95–2.25(1H, m), 2.37(3H,s), 2.66(1H,ddd,J=7&5&2 Hz), 2.98(2H,t, J=6.5 Hz), 3.7–3.85(2H,m), 4.0–4.3(4H,m), 4.63(1H,t,J=5 Hz), 5.64(1H,dt,J=11.5&7 Hz), 6.48(1H,br d,J=11.5 Hz), 6.85(2H,d,J=9 Hz), 7.22(2H,d,J=9 Hz), 7.35–7.5(3H,m), 7.9–8.0(2H,m).

REFERENCE EXAMPLE 32

A mixture of (Z)-2-[3-[4-[2-(5-methyl-2-phenyl-4-oxazolyl)ethoxy]phenyl]-2-propenyl]-1,3-dioxane (5.0 g), palladium-carbon (5%, 0.1 g) and ethanol (100 ml) was subjected to catalytic hydrogenation at room temperature under one atmospheric pressure. The catalyst was filtered off, and the filtrate was concentrated under reduced pressure. The concentrate was purified by means of a silica gel column chromatography. From the fractions eluted with hexane-ethyl acetate (1:1), 2-[3-[4-[2-(5-methyl-2-phenyl-4-oxazolyl)ethoxy]phenyl]propyl]-1,3-dioxane (4.8 g, 96%) was obtained.

NMR (δ ppm in $CDCl_3$): 1.25–1.4(1H,m), 1.5–1.8(4H, m), 1.9–2.2(1H,m), 2.37(3H,s), 2.54(2H,t,J=7 Hz), 2.96(2H, t,J=6.5 Hz), 3.65–3.85(2H,m), 4.0–4.15(2H,m), 4.21(2H,t, J=6.5 Hz), 4.50(1H,t,J=5 Hz), 6.80(2H,d,J=9 Hz), 7.06(2H, d,J=9 Hz), 7.35–7.5(3H,m), 7.9–8.0(2H,m).

REFERENCE EXAMPLE 33 TO REFERENCE EXAMPLE 36

In substantially the same manner as in Reference Example 1, compounds shown in [Table 10] were obtained.

TABLE 10

R—O—⟨C6H4⟩—CH=CHCOOC2H5 (E)

| Reference Example No. | R | Yield (%) | m.p. (° C.) | Recrystallization solvent |
|---|---|---|---|---|
| 33 | 4-methylphenyl-oxazole-CH2CH2— (2-(4-methylphenyl)-5-methyl-oxazol-4-yl-CH2CH2—) | 88 | 126–127 | diethyl ether-isopropyl ether |
| 34 | 2-naphthyl-oxazole-CH2CH2— (2-(2-naphthyl)-5-methyl-oxazol-4-yl-CH2CH2—) | 86 | 111–112 | dichloromethane-isopropyl ether |
| 35 | 2-ethyl-5-methyl-oxazol-4-yl-CH2CH2— | 89 | oily product[1] | |
| 36 | 2-phenyl-5-methyl-oxazol-4-yl-CH2— | 96 | 145–146 | ethyl acetate-hexane |

Note
[1]NMR(δ ppm in $CDCl_3$): 1.30(3H, t, J=7.5Hz), 1.33(3H, t, J=7Hz), 2.25(3H, s), 2.70(2H, q, J=7.5Hz), 2.88(1H, t, J=7Hz), 4.20(2H, t, J=7Hz), 4.25(2H, q, J=7.5Hz), 6.29(1H, d, J=16Hz), 6.88 (2H, d, J=9Hz), 7.45(2H, d, J=9Hz), 7.63(1H, d, J=16Hz).

REFERENCE EXAMPLE 37

In substantially the same manner as in Reference Example 1, by reaction of 5-formyl-2-(5-methyl-2-phenyl-4-oxazolylmethyl)benzofuran with triethyl phosphonoacetate, was obtained ethyl (E)-3-[2-(5-methyl-2-phenyl-4-oxazolylmethyl)benzofuran-5-yl]acrylate. Yield was 74%. Recrystallization from ether-hexane gave colorless prisms, m.p. 150–151° C.

REFERENCE EXAMPLE 38

In substantially the same manner as in Reference Example 1, by reaction of (E)-4-[2-(5-methyl-2-phenyl- 4-oxazolyl)ethoxy]cinnamaldehyde with triethyl phosphonoacetate, was obtained ethyl (E)-5-[4-[2-(5-methyl-2-phenyl-4-oxazolyl)ethoxy]phenyl]-2,4 -pentadienoate. The yield was 56%. Recrystallization from ether-hexane gave colorless needles, m.p. 102–103° C.

REFERENCE EXAMPLE 39

A mixture of 4-(5-methyl-2-phenyl-4-oxazolylmethoxy) benzaldehyde (2.9 g), sodium pyruvate (3.3 g), sodium carbonate (3.2 g), water (80 ml) and methanol (80 ml) was stirred for 6 hours under reflux. The reaction mixture was concentrated under reflux to about ⅓ of the initial volume. The concentrate was subjected to extraction with ethyl acetate. The aqueous layer was acidified with conc. HCl. Resulting crystalline precipitate was collected by filtration to obtain (E)-4-(5-methyl-2-phenyl-4-oxazolylmethoxy) benzylidenepyruvic acid (1.6 g, 44%). Recrystallization from chloroform-methanol gave colorless needles, m.p.197–198° C.

REFERENCE EXAMPLE 40

To a mixture of (E)-4-(5-methyl-2-phenyl-4-oxazolylmethoxy)benzylidenepyruvic acid (1.3 g) and ethanol (50 ml) was added conc. sulfuric acid (0.1 ml). The mixture was heated for 8 hours under reflux, then the reaction mixture was poured into water, which was subjected to extraction with ethyl acetate. The ethyl acetate layer was washed with water and dried ($MgSO_4$), followed by distilling off the solvent. The residue was subjected to a silica gel column chromatography. From the fractions eluted with ethyl acetate-hexane (1:3, v/v), ethyl (E)-4-(5-methyl-2-phenyl-4-oxazolylmethoxy)benzylidenepyruvate (1,2 g, 86%) was obtained. Recrystallization from ethyl acetate-hexane gave pale yellow prisms. Melting point: 110–111° C.

REFERENCE EXAMPLE 41

In substantially the same manner as in Reference Example 22, from ethyl (E)-4-(5-methyl-2-phenyl-4-oxazolylmethoxy)benzylidenepyruvate, was obtained ethyl 2-hydroxy-4-[4-(5-methyl-2-phenyl-4-oxazolylmethoxy] phenyl]butyrate. The yield was 89%. NMR (δ ppm $CDCl_3$): 1.28(3H,t,J=7 Hz), 1.8–2.2(2H,m), 2.43(3H,s), 2.71(2H,t, J=7 Hz), 2.84(1H,d,J=5.2 Hz), 4.1–4.3(1H,m), 4.21(2H,q, J=7 Hz), 4.97(2H,s), 6.94(2H,d,J=9 Hz), 7.13(2H,d,J=9 Hz), 7.4–7.5(3H,m), 7.95–8.1(2H,m).

REFERENCE EXAMPLE 42 TO REFERENCE EXAMPLE 45

In substantially the same manner as in Reference Example 7, compounds shown in [Table 11] were obtained.

TABLE 11

R—O—⟨phenyl⟩—CH=CHCH₂OH (E)

| Reference Example No. | R | Yield (%) | m.p. (° C.) | Recrystallization solvent |
|---|---|---|---|---|
| 42 | 4-methylphenyl-2-yl-5-methyloxazol-4-yl-CH₂CH₂— | 84 | 123–124 | dichloromethane-isopropyl ether |
| 43 | naphthalen-2-yl-2-yl-5-methyloxazol-4-yl-CH₂CH₂— | 81 | 134–135 | dichloromethane-isopropyl ether |

TABLE 11-continued

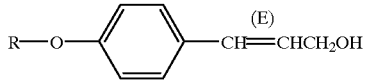

| Reference Example No. | R | Yield (%) | m.p. (° C.) | Recrystallization solvent |
|---|---|---|---|---|
| 44 | [2-ethyl-5-methyl-oxazol-4-yl with CH₂CH₂—] | 34 | oily product[1] | |
| 45 | [2-phenyl-5-methyl-oxazol-4-yl with CH₂—] | 97 | 133–134 | ethyl acetate-hexane |

Note
NMR(δ ppm in CDCl₃): 1.30(3H, t, J=7.5Hz), 1.3–1.5(1H, m), 2.45(3H, s), 2.70(2H, q, J=7.5Hz), 2.87(2H, t, J=7Hz), 4.17(2H, t, J=7Hz), 4.25–4.35(2H, m), 6.23(1H, dt, J=16&6Hz), 6.55(1H, d, J=16Hz), 6.83(2H, d, J=9Hz), 7.30(2H, d, J=9Hz).

REFERENCE EXAMPLE 46

In substantially the same manner as in Reference Example 7, ethyl (E)-3-[2-(5-methyl-2-phenyl-4-oxazolyl methyl)benzofuran-5-yl]acrylate was subjected to reduction to give (E)-3-[2-(5-methyl-2-phenyl-4-oxazolylmethyl)benzofuran-5-yl]-2-propen-1-ol. The yield was 57%. Recrystallization from dichloromethane-hexane gave colorless needles, m.p. 156–157° C.

REFERENCE EXAMPLE 47

In substantially the same manner as in Reference Example 7, ethyl (E,E)-5-[4-[2-(5-methyl-2-phenyl-4-oxazolyl) ethoxy]phenyl]-2,4-pentadienoate was subjected to reduction to give (E,E)-5-[4-[2-(5-methyl-2-phenyl- 4-oxazolyl) ethoxy]phenyl]-2,4-pentadien-1-ol. The yield was 63%. Recrystallization from dichloromethane-hexane gave colorless scales, m.p.132–133° C.

REFERENCE EXAMPLE 48 TO REFERENCE EXAMPLE 51

In substantially the same manner as in Reference Example 14, compounds shown in [Table 12] were obtained.

TABLE 12

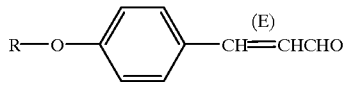

| Reference Example No. | R | Yield (%) | m.p. (° C.) | Recrystallization solvent |
|---|---|---|---|---|
| 48 | [2-(4-methylphenyl)-5-methyl-oxazol-4-yl with CH₂CH₂—] | 84 | 115–116 | dichloromethane-isopropyl ether |

TABLE 12-continued

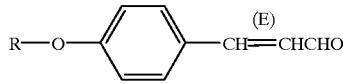

| Reference Example No. | R | Yield (%) | m.p. (° C.) | Recrystallization solvent |
|---|---|---|---|---|
| 49 | 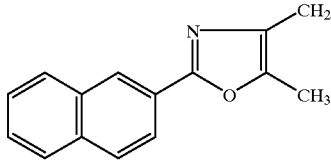 | 91 | 155–156 | dichloromethane-isopropyl ether |
| 50 | 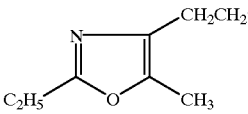 | 95 | oily product[1] | |
| 51 | 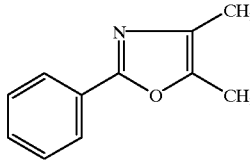 | 70 | 114–115 | ethyl acetate-hexane |

Note
[1]NMR(δ ppm in CDCl$_3$): 1.30(3H, t, J=7.5Hz), 2.25(3H, s), 2.71(2H, q, J=7.5Hz), 2.90(2H, t, J=6.5Hz), 4.23(2H, t, J=6.5Hz), 6.60(1H, dd, J=16&7.5Hz), 6.93(2H, d, J=9Hz), 7.41(1H, d, J=16Hz), 7.50(2H, d, J=9Hz), 9.65(1H, d, J=7.5Hz).

REFERENCE EXAMPLE 52

In substantially the same manner as in Reference Example 14, from (E)-3-[2-(5-methyl-2-phenyl-4-oxazolylmethyl)benzofuran-5-yl]-2-propen-1-ol, was obtained (E)-3-[2-(5-methyl-2-phenyl-4-oxazolylmethyl)benzofuran-5-yl] acrolein. The yield was 93%. Recrystallization from dichloromethane-hexane gave colorless needles, m.p.136–137° C.

REFERENCE EXAMPLE 53

In substantially the same manner as in Reference Example 14, from (E,E)-5-[4-[2-(5-methyl-2-phenyl-4-oxazolyl)ethoxy]phenyl]-2,4-pentadien-1-ol, was obtained (E,E)-5-[4-[2-(5-methyl-2-phenyl-4-oxazolyl)ethoxy]phenyl]-2,4-pentadien-1-al. The yield was 82%. Recrystallization from dichloromethane-hexane gave yellow prisms, m.p.133–134° C.

REFERENCE EXAMPLE 54

A mixture of 4-bromoacetyl-5-methyl-2-phenyloxazole (2.60 g), 4-[2-(1,3-dioxolan-2-yl)ethyl]phenol (1.82 g), potassium carbonate (1.28 g) and 2-butanone (60 ml) was stirred for 20 hours at temperatures ranging from 70 to 80° C. The reaction mixture was poured into water. Resulting crystalline precipitate was collected by filtration, which was purified by means of a silica gel column chromatography. From the fractions eluted with chloroform-methanol (100:1, v/v), 4-[4-[2-(1,3-dioxolan-2-yl)ethyl]phenoxyacetyl]-5-methyl-2-phenyloxazole (2.08g, 57%) was obtained. Recrystallization from dichloromethane-isopropyl ether gave colorless prisms, m.p.119–120° C.

REFERENCE EXAMPLE 55

In substantially the same manner as in Reference Example 1, ethyl 4-[2-[N-methyl-N-(2-pyridyl)amino]-ethoxy] cinnamate was obtained. Yield: 97%. Recrystallization from dichloromethane-isbpropyl ether gave colorless prisms. Melting point 80–81° C.

REFERENCE EXAMPLE 56

In substantially the same manner as in Reference Example 1, ethyl (E)-3-[2-(5-methyl-2-phenyl-4-oxazolylmethoxy)-5-pyridyl]acrylate was obtained. Yield: 86%. Recrystallization from dichloromethane-isopropyl ether gave colorless prisms. Melting point: 109–110° C.

REFERENCE EXAMPLE 57

In substantially the same manner as in Reference Example 7, (E)-3-[4-[2-[N-methyl-N-(2-pyridyl)amino]ethoxy]phenyl]-2-propen-1-ol was obtained as an oily substance. Yield: 87%.

NMR (δ ppm in CDCl$_3$): 3.14(3H,s), 3.98(2H,t,J=5.5 Hz), 4.19(2H,t,J=5.5 Hz), 4.29(2H,br d, J=5.5 Hz), 6.22(1H,dt, J=16&6 Hz), 6.45–6.6(3H,m), 6.85(2H,d,J=9 Hz), 7.30(2H, d,J=9 Hz), 7.45(1H,ddd,J=8.5&7&2 Hz), 8.1–8.2(1H,m).

REFERENCE EXAMPLE 58

In substantially the same manner as in Reference Example 7, (E)-3-[2-(5-methyl-2-phenyl-4-oxazolyl-methoxy)-5-pyridyl]-2-propen-1-ol was obtained. Yield: 57%. Recrystallization from dichloromethane-isopropyl ether gave colorless prisms. Melting point: 116–117° C.

REFERENCE EXAMPLE 59

In substantially the same manner as in Reference Example 14, 4-[2-[N-methyl-N-(2-pyridyl)amino]-ethoxy] cinnamaldehyde was obtained as an oily substance. Yield: 100%.

NMR (δ ppm in CDCl$_3$): 3.15(3H,s), 4.01(2H,t,J=5.5 Hz), 4.25(2H,t,J=5.5 Hz), 6.5–6.7(3H,m), 6.95(2H,d,J=9 Hz), 7.41(1H,d,J=16 Hz), 7.4–7.55(3H,m), 8.16(1H,ddd,J=5&2&1 Hz), 9.65(1H,d,J=8 Hz).

REFERENCE EXAMPLE 60

In substantially the same manner as in Reference Example 14, (E)-3-[2-(5-methyl-2-phenyl-4-oxazolyl-methoxy)-5-pyridyl]acrolein was obtained. Yield: 92%. Recrystallization from dichloromethane-isopropyl ether gave colorless prisms. Melting point: 147–148° C.

REFERENCE EXAMPLE 61

A solution of n-butyllithium in hexane (1.62M, 25.9 ml) was added dropwise to a suspension of [2-(1,3-dioxolan-2-yl)ethyl]triphenylphosphonium bromide (18.6 g) in tetrahydrofuran (180 ml) at –20° C. The mixture was stirred for 2 hours. To the reaction mixture was added 4-[2-(2-naphthyl)-5-methyl-4-oxazolylmethoxy]benzaldehyde (12.0 g). The mixture was stirred at 50-55° C. for 4 hours. The reaction mixture was poured into ice-water, followed by subjecting extraction with ethyl acetate.

The ethyl acetate layer was washed with 0.1N-hydrochloric acid and water in the order mentioned and dried over magnesium sulfate. The solvent was distilled off. The residue was subjected to silica gel column chromatography. From the fraction eluted with chloroform-methanol (100:5), crystals (14.8 g) were obtained. The crystals were dissolved in tetrahydrofuran (250 ml). To the solution was added palladium-carbon (5%, 3.0 g). The mixture was subjected to catalytic hydrogenation at room temperature under atmospheric pressure. The catalyst was filtered off. The filtrate was concentrated under reflux, whereby 4-[4-[3-(1,3-dioxolan-2-yyl)propyl]phenoxymethyl]-5-methyl-2-(2-naphthyl)oxazole (12.1 g, 81%) was obtained. Recrystallization from dichloromethane-isopropyl ether gave colorless prisms. Melting point: 141-142° C. Reference Example 62 In substantially the same manner as in Reference Example 1, ethyl (E)-4-hydroxy-3-nitrocinnamate was obtained by reacting 4-hydroxy-3-nitrobentaldehyde with triethyl phosphonoacetate. Recrystallization from dichloromethane-isopropyl ether gave pale yellow needles. Melting point: 114–115° C.

REFERENCE EXAMPLE 63

In substantially the same manner as in Reference Example 24, ethyl 3-(3-amino-4-hydroxyphenyl)propionate was obtained as an oily substance by subjecting ethyl (E)-4-hydroxy-3-nitrocinnamate to catalytic reduction. NMR (δ ppm in CDCl$_3$): 1.24(3H,t,J=7 Hz), 2.5–2.9(4H,m), 4.12 (2H,q,J=7 Hz), 6.49(1H,dd,J=8&2 Hz), 6.60(1H,d,J=2 Hz), 6.64(1H,d,J=8 Hz).

REFERENCE EXAMPLE 64

A mixture of phosphorus pentoxide (P$_2$O$_5$) (12.9 g), hexamethyldisiloxane (29.5 g) and 1,2-dichlorobenzene was heated for 10 minutes under reflux. To the mixture were added ethyl 3-(3-amino-4-hydroxyphenyl)propionate (4.75 g) and 2-naphthylacetic acid (4.23 g). The mixture was heated for 3 hours under reflux. The reaction mixture was poured into water and allowed to extraction with ethyl acetate. The ethyl acetatae layer was washed with water and dried over magnesium sulfate. The solvent was distilled off, and the residue was subjected to silica gel column chromatography. From the fractions eluted with ethyl acetate-hexane (1:4, v/v), ethyl 3-[2-(2-naphthylmethyl) benzoxazol-5-yl]propionate (5.95 g, 73%) was obtained. Recrystallization from ether-isopropyl ether gave colorless needles. Melting point: 81–82° C.

REFERENCE EXAMPLE 65

To a solution of ethyl 3-[2-(2-naphthylmethyl)-benzoxazol-5-yl]propionate (5.8 g) in ether (100 ml)-tetrahydrofuran (100 ml) was added lithium aluminum hydride (0.73 g), and the mixture was stirred at room temperature for one hour. To the reaction mixture was added water (4 ml). Insolubles were filtered off. The filtrate was concentrated under reduced pressure, and the residue was subjected to silica gel column chromatography. From the fraction eluted with ethyl acetate-hexane (1:1, v/v), 3-[2-(2-naphthylmethyl)benzoxazol-5-yl]propanol (2.1 g, 41%) was obtained. Recrystallization from dichloromethane-isopropylether gave colorless prisms. Melting point: 102–103° C.

REFERENCE EXAMPLE 66

Oxalyl chloride[(COCl)$_2$] (0.88 g) was added dropwise to a solution of dimethyl sulfoxide (DMSO) (1.0 g) in dichloromethane (30 ml) at –30° C. To the mixture was added 3-[2-(2-naphthylmethyl)benzoxazol-5-yl]-propanol (2.0 g). The mixture was stirred for 30 minutes at the same temperature. To the mixture was added triethyl amine (3.19 g). The mixture was stirred for 30 minutes, warmed to 0° C. and poured into 2N HCl. The organic layer was separated, washed with water and dried over magnesium sulfate (MgSO$_4$). The solvent was distilled off, and the residue was subjected to silica gel column chromatography. From the fractions eluted with ethyl acetate-hexane (1:2, v/v), 3-[2-(2-naphthylmethyl)benzoxazol-5-yl]propionaldehyde (1.54 g, 77%) was obtained. Recrystallization from ether-isopropyl ether gave colorless needles. Melting point: 81–82° C.

REFERENCE EXAMPLE 67

A mixture of 3-[2-(2-naphthylmethyl)benzoxazol-5-yl] propionaldehyde (2.9 g), ethylene glycol (0.685 g), P-toluenesulfonic acid monohydrate (0.175 g) and benzene (50 ml) was stirred for 3 hours under reflux. The reaction mixture was successively washed with aqueous solution of sodium hydrogencarbonate and water, and dried over magnesium sulfate (MgSO4). The solvent was distilled off, whereby 5-[2-(1,3-dioxolan-2-yl)ethyl]-2-(2-naphthylmethyl)benzoxazole (2.95 g, 89%) was obtained. Recrystallization from dichloromethane- isopropyl ether gave colorless prisms. Melting point: 85–86° C.

REFERENCE EXAMPLE 68

A mixture of 2-chloromethyl-5-methyl-2-phenyloxazole (20.8 g), 3-hydroxybenzaldehyde (12.2 g), potassium carbonate (27.6 g) and N,N-dimethylformamide (DMF) (200 ml) was heated at 90° C. for 2 hours. The reaction mixture was poured into water, and subjected to extraction with ethyl acetate. The ethyl acetate layer was washed with water and dried over magnesium sulfate (MgSO$_4$). The solvent was distilled off, whereby 3-(5-methyl-2-phenyl-4-oxazolylmethoxy)benzaldehyde (26.5 g, 90%) was obtained. Recrystallization from ethanol gave colorless prisms. Melting point: 67–68° C.

REFERENCE EXAMPLE 69

In substantially the same manner as in Reference Example 1, ethyl (E)-3-(5-methyl-2-phenyl-4-oxazolylmethoxy)cinnamate was obtained. Recrystallization from ethanol gave colorless prisms. Melting point: 91–92° C.

REFERENCE EXAMPLE 70

To a solution of ethyl (E)-3-(5-methyl-2-phenyl-4-oxazolylmethoxy)cinnamate (14.0 g) in dichloromethane (200 ml) was added a solution of diisobutylaluminium hydride in toluene (1.5M, 51 ml) dropwise under ice cooling. The reaction mixture was stirred for 30 minutes at the same temperature, and to the mixture was added dropwise 2N-HCl (150 ml). The organic layer was separated, washed with water and dried over magnesium sulfate ($MgSO_4$). The solvent was distilled off, whereby (E)-[3-(5-methyl-2-phenyl-4-oxazolylmethoxy)phenyl]-2-propen-1-ol (11.5 g, 92%) was obtained. Recrystallization from ethyl acetate gave colorless prisms. Melting point: 120–121° C.

REFERENCE EXAMPLE 71

In substantially the same manner as in Reference Example 14, (E)-3-(5-methyl-2-phenyl-4-oxazolylmethoxy)cinnamaldehyde was obtained. Recrystallization from ethanol acetate-hexane gave colorless rods. Melting point: 103–104° C.

REFERENCE EXAMPLE 72

In substantially the same manner as in Reference Example 23, 2-(5-methyl-2-phenyl-4-oxazolylmethoxy)-5-nitropyridine was obtained. Recrystallization from dichloromethane-isopropyl ether gave pale yellow prisms. Melting point: 142–143° C.

REFERENCE EXAMPLE 73

In substantially the same manner as in Reference Example 24, 5-amino-2-(5-methyl-2-phenyl-4-oxazolylmethoxy)pyridine was obtained. Recrystallization from methanol-isopropyl ether gave colorless prisms. Melting point: 106–107° C.

REFERENCE EXAMPLE 74

In substantially the same manner as in Reference Example 25, 5-iodo-2-(5-methyl-2-phenyl-4-oxazolylmethoxy)pyridine was obtained. Recrystallization from ethyl-acetate gave colorless prisms. Melting point: 129–130° C.

REFERENCE EXAMPLE 75

In substantially the same manner as in Reference Example 26, 5-formyl-2-(5-methyl-2-phenyl-4-oxazolylmethoxy)pyridine was obtained. Recrystallization from ethyl acetate-hexane gave colorless prisms. Melting point: 116–117° C.

REFERENCE EXAMPLE 76

To a mixture of 4-benzyloxybenzaldehyde (4.5 g), (1,3-dioxolan-2-ylmethyl)triphenylphosphonium bromide and N,N-dimethylformamide (DMF) (50 ml) was added sodium hydride (60% in oil, 0.935 g). The mixture was stirred for 3 hours at 60° C. The reaction mixture was poured into ice-water and neutralized with 2N-HCl. The mixture was subjected to extraction with ethyl acetate. The ethyl acetate layer was washed with water and dried over magnesium sulfate ($MgSO_4$). The solvent was distilled off, and the residue was subjected to silica gel column chromatography. From the fractions eluted with chloroform, 2-vinyl-1,3-dioxolane derivative (5.7 g) was obtained as an oily substance. The oily substance was dissolved in ethanol (150 ml). To the solution was added palladium-carbon (5%, 2.0 g), and the mixture was subjected to catalytic hydrogenation at room temperature under atmospheric pressure. The catalyst was filtered off, and the filtrate was concentrated under reduced pressure. The residue was subjected to silica gel column chromatography. From the fractions eluted with chloroform-ethyl acetate (50:1, v/v), 2-[2-(4-hydroxyphenyl)ethyl]-1,3-dioxolane was obtained as an oily substance.

NMR (δ ppm in $CDCl_3$): 1.85–2.0(2H,m), 2.6–2.75(2H,m), 3.8–4.15(4H,m), 4.82(1H,broad s), 4.88(1H,t,J=4.5 Hz), 6.75(2H,d,J=8.5 Hz), 7.07(2H,d,J=8.5 Hz).

REFERENCE EXAMPLE 77

In substantially the same manner as in Reference Example 1, crude ethyl (E)-4-isopropoxycinnamate was obtained. The crude substance was subjected to silica gel column chromatography, and eluted with ether-hexane (1:5, v/v).

NMR (δ ppm in $CDCl_3$): 1.33(3H,t,J=7 Hz), 1.35(6H,d,J=6 Hz), 4.25(2H,q,J=7 Hz), 4.5–4.7(1H,m), 6.30(1H,d,J=16 Hz), 6.87(2H,d,J=9 Hz), 7.46(2H,d,J=9 Hz), 7.63(1H,d,J=16 Hz).

REFERENCE EXAMPLE 78

In substantially the same manner as in Reference Example 7, crude (E)-3-(4-isopropoxyphenyl)-2-propen-1-ol was obtained. The crude substance was subjected to silica gel column chromatography, and eluted with ethyl acetate-hexane (1:4, v/v).

NMR (δ ppm in $CDCl_3$): 1.33(6H,d,J=6 Hz), 1.38(1H,t,J=6 Hz), 4.30(2H,dt,J=6&1.5 Hz), 4.45–4.65(1H,m), 6.23(1H,dt,J=16&6 Hz), 6.56(1H,d,J=16 Hz), 6.84(2H,d,J=8.5 Hz), 7.31(2H,d,J=8.5 Hz).

REFERENCE EXAMPLE 79

In substantially the same manner as in Reference Example 14, (E)-4-isopropoxycinnamaldehyde was obtained as an oily substance.

NMR (δ ppm in $CDCl_3$): 1.37(6H,d,J=6 Hz), 4.5–4.7(1H,m), 6.61(1H,dd,J=16&8 Hz), 6.92(2H,d,J=9 Hz), 7.42(1H,d,J=16 Hz), 7.51(2H,d,J=9 Hz).

REFERENCE EXAMPLE 80

To a solution of 5-[3-(4-isopropoxyphenyl)propyl]-2,4-oxazolidinedione (1.5 g) in dichloromethane (70 ml) was added dropwise titanium tetrachloride ($TiCl_4$) (4.1 g) at 0° C. The mixture was stirred for one hour at the same temperature. The reaction mixture was poured into ice-water, and subjected to extraction with ethyl acetate. The ethyl acetate layer was washed with water and dried over magnesium sulfate ($MgSO_4$). The solvent was distilled off, and the residue was subjected to silica gel column chromatography. From the fractions eluted with ethyl acetate-hexane (1:4, v/v), 5-[3-(4-hydroxyphenyl)propyl]-2,4-oxazolidinedione (0.755 g, 59%) was obtained. Recrystallization from acetone-hexane gave colorless prisms. Melting point: 132–133° C.

REFERENCE EXAMPLE 81

To a mixture of 4-isopropoxybenzaldehyde (15.0 g), triethyl 4-phosphonocrotonate (27.3 g) and N,N-dimethylformamide (DMF) (100 ml) was added oily sodium hydride (60%, 4.38 g), and the mixture was stirred for 16 hours at room temperature. The reaction mixture was poured into ice-water, and neutralized with 2N-HCl. The mixture was subjected to extraction with ethyl acetate. The ethyl acetate layer was washed with water and dried over magnesium sulfate ($MgSO_4$). The solvent was distilled off and the residue was subjected to column chromatography. From the fractions eluted with ether-hexane, ethyl (E,E)-5-(4-isopropoxyphenyl)-2,4-pentadienoate (13.7 g, 58%) was obtained. Recrystallization from ether-hexane gave colorless prisms. Melting point 64–65° C.

REFERENCE EXAMPLE 82

In substantially the same manner as in Reference Example 7, ethyl (E,E)-5-(4-isopropoxyphenyl)-2,4-pentadienate was reduced with diisobutylaluminium hydride to give (E,E)-5-(4-isopropoxyphenyl)-2,4-pentadien-1-ol. Recrystallization from isopropyl ether gave colorless needles. Melting point 91–92° C.

REFERENCE EXAMPLE 83

In substantially the same manner as in Reference Example 14, (E,E)-5-(4-isopropoxyphenyl)-2,4-pentadien-1-ol was oxidized with manganese dioxide to give (E,E)-5-(4-isopropoxyphenyl)-2,4-pentadien-1-al as an oily substance.

NMR (δ ppm in $CDCl_3$): 1.36(6H,d,J=6 Hz), 4.5–4.7(1H, m), 6.22(1H,dd,J=15&8 Hz), 6.8–7.05(4H,m), 7.26(1H,dd, J=J=15&10 Hz), 7.44(2H,d,J=9 Hz), 9.59(1H,d,J=8 Hz).

REFERENCE EXAMPLE 84

In substantially the same manner as in Reference Example 80, 5-[5-(4-hydroxyphenyl)pentyl]-2,4-oxazolidinedione was obtained. Recrystallization from ether-isopropyl ether gave colorless prisms. Melting point: 96–97° C.

REFERENCE EXAMPLE 85

To an ice-cooled solution of [2-(1,3-dioxolan-2-yl)ethyl] triphenylphosphonium bromide (51,0 g) in N,N-dimethylformamide (DMF) (200 ml) was added portionwise sodium hydride (60% in oil, 4.6 g), and the mixture was stirred for 15 minutes. To the mixture was added 4-isopropoxybenzaldehyde (18.0 g), and the mixture was stirred for 5 hours at 80–85° C. The reaction mixture was poured into ice water, and neutralized with 2N-HCl. The mixture was subjected to extraction with ether. The ether layer was washed with water and dried over magnesium sulfate. The solvent was distilled off and the residue was subjected to silica gel column chromatography. From the fractions eluted with ethyl acetate-hexane (1:4, v/v), 1,3-dioxolane derivative (14.5 g) was obtained as an oily substance.

The oily substance was dissolved in ethanol (250 ml). By using palladium-carbon (5%, 5.0 g) as catalyst, the solution was subjected to catalytic reduction at room temperature and atmospheric pressure. The catalyst was filtered off and the filtrate was concentrated under reduced pressure. The residue was subjected to silica gel column chromatography. From the fractions eluted with ethyl acetate-hexane (1:5, v/v), 2-[3-(4-isopropoxyphenyl)propyl]-1,3-dioxolane (6.7 g, 24%) was obtained as an oily substance.

NMR (δ ppm in $CDCl_3$): 1.32(6H,d,J=6 Hz), 1.6–1.8(4H, m), 2.5–2.65(2H,m), 3.8–4.0(4H,m), 4.4–4.6(1H,m), 4.8–4.9(1H,m), 6.8(2H,d,J=8.5 Hz), 7.07(2H,d,J=8.5 Hz).

REFERENCE EXAMPLE 86

In substantially the same manner as in Reference Example 80, 5-[4-(4-hydroxyphenyl)butyl]-2,4-oxazolidinedione was obtained. Recrystallization from dichloromethane-methanol gave colorless prisms.

Melting point: 151–152° C.

REFERENCE EXAMPLE 87

In substantially the same manner as in Reference Example 68, 4-(5-methyl-2-phenyl-4-oxazolylmethoxy) acetophenone was obtained by reaction of 4-chloromethyl-5-methyl-2-phenyloxazole with p-hydroxyacetophenone. Recryatallization of ethyl acetate-hexane gave colorless crystals.

Melting point: 126–127° C.

REFERENCE EXAMPLE 88

In substantially the same manner as in Reference Example 1, methyl (E)-3-[4-(5-methyl-2-phenyl-4-oxazolylmethoxy) phenyl]-2-butenoate was obtained by reaction of 4-(5-methyl-2-phenyl-4-oxazolylmethoxy) acetophenone with trimethyl phophonoacetate. Recryatallization of ethyl acetate-ether gave colorless crystals.

Melting point: 125–126° C.

REFERENCE EXAMPLE 89

In substantially the same manner as in Reference Example 7, methyl (E)-3-[4-(5-methyl-2-phenyl-4-oxazolylmethoxy) phenyl]-2-buten-1-ol was obtained by reduction of methyl (E)-3-[4-(5-methyl-2-phenyl-4 -oxazolylmethoxy)phenylj-2-butenoate-with diisobutylaluminum hydride. Recrystallization of ethyl acetate-ether gave colorless crystals.

Melting point: 126–127° C.

REFERENCE EXAMPLE 90

In substantially the same manner as in Reference Example 14, methyl (E)-3-[4-(5-methyl-2-phenyl-4-oxazolylmethoxy)phenyl]-2-buten-1-al was obtained by oxidation of (E)-3-(4-(5-methyl-2-phenyl-4-oxazolylmethoxy)phenyl]-2-buten-1-ol with manganese dioxide. Recryatallization of ethyl acetate-ether gave colorless crystals.

Melting point: 94–95° C.

What is claimed is:

1. 5-[3-[4-(5-methyl-2-phenyl-4-thiazolylmethoxy) phenyl]propyl]-2,4-oxazolidinedione or a salt thereof.
2. A medicinal composition comprising, as the effective component, the compound of claim 1 and a pharmaceutically acceptable carrier.
3. A method for treating a mammal suffering from diabetes, comprising administering to a mammal in need thereof an effective amount of the compound of claim 1.
4. A method for treating a mammal suffering from hyperlipidemia, comprising administering to a mammal in need thereof an effective amount of the compound of claim 1.

5. A method of producing the compound of claim 1, comprising reacting a compound of the formula:
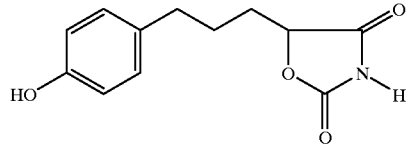
with a compound represented by the general formula:
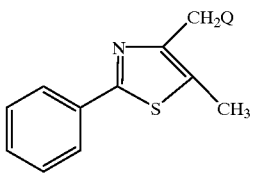
wherein Q is a leaving group.
* * * * *